US009447384B2

(12) United States Patent
Cass et al.

(10) Patent No.: US 9,447,384 B2
(45) Date of Patent: Sep. 20, 2016

(54) MODIFIED ARSENITE OXIDASE AND A BIOSENSOR FOR DETECTING ARSENITE

(71) Applicant: The Bio Nano Centre Limited, London (GB)

(72) Inventors: Anthony Edward George Cass, London (GB); Joanne Santini, London (GB); Christopher James Johnson, London (GB)

(73) Assignee: The Bio Nano Centre Limited (GB)

( * ) Notice: Subject to any disclaimer, the term of this patent is extended or adjusted under 35 U.S.C. 154(b) by 73 days.

(21) Appl. No.: 14/352,437

(22) PCT Filed: Oct. 19, 2012

(86) PCT No.: PCT/GB2012/052609
§ 371 (c)(1),
(2) Date: Apr. 17, 2014

(87) PCT Pub. No.: WO2013/057515
PCT Pub. Date: Apr. 25, 2013

(65) Prior Publication Data
US 2014/0238857 A1 Aug. 28, 2014

(30) Foreign Application Priority Data

Oct. 19, 2011 (GB) .................................. 1118026.2

(51) Int. Cl.
*C12Q 1/26* (2006.01)
*G01N 27/447* (2006.01)
*C12N 9/02* (2006.01)
*C12Q 1/00* (2006.01)

(52) U.S. Cl.
CPC ............. *C12N 9/0004* (2013.01); *C12Q 1/005* (2013.01); *C12Q 1/26* (2013.01); *C12Y 120/09001* (2013.01); *C12Y 120/99001* (2013.01); *G01N 27/447* (2013.01)

(58) Field of Classification Search
None
See application file for complete search history.

(56) References Cited

FOREIGN PATENT DOCUMENTS

WO     0229007 A2   4/2002

OTHER PUBLICATIONS

Marchal et al. (Microbiology, Effect of arsenite on swimming motility delays surface colonization in Herminiimonas arsenicoxydans, Aug. 2010;156(Pt 8):2336-42).*
Lleutaud et al. (Arsenite Oxidase from Ralstonia sp. 22, The Journal of Biological Chemistry vol. 285, No. 27, pp. 20433-20441, Jul. 2, 2010).*

Atschul et al., "Gapped BLAST and PSI-BLAST: a new generation of protein database search programs", Nucleic Acids Res., 25: 3389-3402 (1997).
Battaglia-Brunet F et al: "An arsenic(III)-oxidizing bacterial population: selection, characterization, and performance in reactors", Journal of Applied Microbiology, Oxford, GB, vol. 93, No. 4, Jan. 1, 2002, pp. 656-667, XP002215222.
D. Malasarn et al: "Characterization of the Arsenate Respiratory Reductase from *Shewanella* sp. Strain ANA-3", Journal of Bacteriology, vol. 190, No. 1, Jan. 1, 2008, pp. 135-142, XP055052315.
Focus, "*Escherichia coli* Strain DH5™ Is a Suitable Host for the Study of PHOA Insertions" (1986) 8:2, 9.
Grant, S.G.N. et al., "Differential plasmid rescue from transgenic mouse DNAs into *Escherichia coli* methylation-restriction mutants", (1990) Proc. Natl. Acad. Sci. USA 87: 4645-4649 PMID 2162051.
Hanahan, D. (1985) In DNA Cloning: A Practical Approach (Glover, D.M., ed.), vol. 1, p. 109, IRL Press.
International Search Report for Application No. PCT/GB2012/052609 dated Feb. 14, 2013.
J. H.T. Luong et al: "Analytical Tools for Monitoring Arsenic in the Environment", The Open Analytical Chemistry Journal, Jan. 1, 2007, pp. 7-14. XP055052321.
J. M. Santini et al: "Molybdenum-Containing Arsenite Oxidase of the Chemolithoautotrophic Arsenite Oxidizer NT-26", Journal of Bacteriology, vol. 186, No. 6, Mar. 2, 2004, pp. 1614-1619, XP055052239.
Keith B. Male et al: "Biosensor for Arsenite Using Arsenite Oxidase and Multiwalled Carbon Nanotube Modified Electrodes", Analytical Chemistry, vol. 79, No. 20, Oct. 1, 2007, pp. 7831-7837, XP055051921.
Lett et al., Unified Nomenclature for Genes Involved in Prokaryotic Aerobic Arsenite Oxidation; J. Bacteriology, Nov. 4, 2011; p. 207-208.
Meselson M. and Yuan R., "DNA Restriction Enzyme from *E. coli*" (1968) Nature 217:1110 PMID. 4868368.
Paul V. Bernhardt: "Exploiting the versatility and selectivity of Mo enzymes with electrochemistry", Chemical Communications, vol. 47, No. 6, Jan. 1, 2011, p. 1663, XP055052324.
Penfold et al., "An improved suicide vector for construction of chromosomal insertion mutations in bacteria", (1992) Gene 118:145-146.
Santini et al. "A New Chemolithoautotrophic Arsenite-Oxidizing Bacterium Isolated from a Gold Mine: Phylogenetic, Physiological, and Preliminary Biochemical Studies" (2000) Appl. Environ. Microbiol. 66, 92-97.
Santini et al: "The NT-26 cytochrome c552 and its role in arsenite oxidation", Biochimica Et Biophysica Acta. Bioenergetics, Amsterdam, NL, vol. 1767, No. 2, Feb. 24, 2007, pp. 189-196, XP005904421.
Stocker et al. "Development of a Set of Simple Bacterial Biosensors for Quantitative and Rapid Measurements of Arsenite and Arsenate in Potable Water" (2003) Environ. Sci. Technol. 37, 4743-4750.

(Continued)

*Primary Examiner* — Suzanne M Noakes
*Assistant Examiner* — Jae W Lee
(74) *Attorney, Agent, or Firm* — Lerner, David, Littenberg, Krumholz & Mentlik, LLP

(57) ABSTRACT

The present invention provides an arsenite oxidase enzyme modified to prevent translocation by modification of a translocation signal sequence. A microorganism modified to express the heterologous arsenite oxidase enzyme is also provided by the invention, together with a device for detecting the presence of arsenite in a sample.

6 Claims, 14 Drawing Sheets

(56) References Cited

OTHER PUBLICATIONS

Vanden Hoven R N et al: "Arsenite oxidation by the heterotroph *Hydrogenophaga* sp. str. NT-14: the arsenite oxidase and its physiological electron acceptor", Biochimica Et Biophysica Acta. Bioenergetics, Amsterdam, NL, vol. 1656, No. 2-3, Jun. 7, 2004, pp. 148-155. XP004514821.

Weeger W et al: "Oxidation of Arsenite to Arsenate by a Bacterium Isolated From an Aquatic Environment", Biometals, Kluwer Academic Publishers, NL, vol. 12, No. 2, Jun. 1, 1999, pp. 141-149, XP000926523.

Yanisch-Perron et al., "Improved MI3 phage cloning vectors and host strains: nucleotide sequences of the M13mp18 and pUC19 vectors" (1985) Gene, 33(1):103-19.

\* cited by examiner

MODIFIED ARSENITE OXIDASE AND A BIOSENSOR FOR DETECTING ARSENITE

CROSS-REFERENCE TO RELATED APPLICATIONS

The present application is a national phase entry under 35 U.S.C. §371 of International Application No. PCT/GB2012/052609 filed Oct. 19, 2012, which claims priority from Great Britain Patent Application No. 1118026.2 filed Oct. 19, 2011, the disclosures of which are incorporated herein by reference.

SEQUENCE LISTING

The instant application contains a Sequence Listing which has been submitted in ASCII format via EFS-Web and is hereby incorporated by reference in its entirety. Said ASCII copy, created on Apr. 15, 2014, is named Sequence Listing for GILJEN 3.3-012 (E) ST25.5XT and is 16,442 bytes in the size.

FIELD OF THE INVENTION

The present invention relates to modified enzymes for detecting the presence of arsenic derivatives, in particular arsenite, and methods for expressing such enzymes in heterologous organisms. The invention is also directed to devices for detecting arsenic, and derivatives thereof, in a sample.

BACKGROUND TO THE INVENTION

It is said that the third major challenge for a sustainable future (together with food security and energy) will be making the best use of limited supplies of pure water for both agricultural use and human consumption, and the remediation of marginal and contaminated water will be essential in achieving this. Already groundwater contamination, resulting from either natural geochemical processes or industrial activities such as mining, is a major problem in many countries.

Arsenic (As) is a groundwater contaminant that is ubiquitous in the environment and the two soluble forms, arsenite ($As^{III}$) and arsenate ($As^V$), are toxic. Anthropogenic activity has resulted in widespread contamination of both soluble forms but $As^{III}$ is prevalent in anoxic environments, including most sources of drinking water. Countries affected include India, Bangladesh, Vietnam, USA, Germany, France, Hungary, Australia, Argentina, Mexico, Canada.

An important aspect of remediation is assessment and monitoring, and whilst laboratory methods exist that demonstrate high specificity and sensitivity (e.g. ICP-MS or HPLC) it is also possible, and indeed desirable, to measure analytes such as arsenite in the field using sensors. Ideally, the sensors should be low-cost, disposable and able to be readily adapted to multiple analytes that are commonly found together in contaminated water.

Many As field test kits are commercially available (e.g. from Industrial Systems, Inc, Hydrodyne) but these only detect total As, rather than the most toxic form, $As^{III}$, which is dominant in anoxic drinking waters. Moreover, because As remediation preferentially removes $As^V$ (e.g. by binding to iron hydroxide) and requires the pre-oxidation of $As^{III}$, it is crucial to determine whether any $As^{III}$ remains in the water. The chemically based arsenic field kits rely on a colorimetric method which reduces the $As^{III}$ and $As^V$ to the gas arsine which reacts with the mercuric bromide test strips. These kits require the training of personnel, are expensive (e.g. Arsenic, Quick II Hydrodyne kit US$4.24 per test and Ultra Low Quick II, Industrial Test Systems, Inc. US$6 per test) and have low sensitivity and reproducibility.

Whole cell biosensors have been developed for the detection of $As^{III}$ by a number of groups (e.g. Stocker et al. (2003) Environ. Sci. Technol. 37, 4743-4750). These methods are all based on colorimetric assays that sometimes require the use of a luminometer. They all use the regulatory mechanism of the *Escherichia coli* arsenic resistance system which detects both $As^{III}$ and antimonite ($Sb^{III}$). The regulatory gene in this system, arsR, is fused to a reporter gene (e.g. luciferase gene, luxB) that when expressed after induction with $As^{III}$ produces a visible signal (e.g. fluorescence).

There are many problems with whole cell based $As^{III}$ biosensors, including: 1) the system is too complex and because of this has a slow response time (i.e. $As^{III}$ must enter cells followed by induction of regulator-reporter gene protein—this can take up to 24 hours for a response); 2) lack of specificity as the system does not discriminate between $As^{III}$ and $Sb^{III}$; 3) incubation temperatures of 30° C. are often required; 4) colorimetric assay often requires use of a luminometer, which is not feasible at most field sites; and 5) use of genetically modified organisms always presents an additional problem. No whole cell biosensors for the detection of $As^{III}$ are commercially available.

A biosensor for $As^{III}$ has been developed using molybdenum-containing arsenite oxidase (known as "Aio" and also previously known as Aro and Aso; see Lett et al., Unified Nomenclature for Genes Involved in Prokaryotic Aerobic Arsenite Oxidation; J. Bacteriology, 4 Nov. 2011; p. 207-208) which is a member of the DMSO reductase family, prepared from chemolithoautotrophic Alphaproteobacterium *Rhizobium* sp. strain NT-26 (Santini et al. (2000) Appl. Environ. Microbiol. 66, 92-97).

$As^{III}$ oxidase catalyses the oxidation of $As^{III}$ to $As^V$ and the suitability of this native enzyme for use as a biosensor has been tested and shown to detect down to 1 ppb $As^{III}$, which is 10 times lower than the recommended WHO MCL (maximum contaminant level) of As in drinking water. Furthermore the native enzyme shows specificity for $As^{III}$ (Male et al. (2007) Anal. Chem. 79, 7831-7837). The biosensor comprises the enzyme directly linked to the surface of a multiwalled carbon nanotube-modified electrode, in which electron transfer proceeds directly from enzyme to electrode. The authors noted, however, that certain commonly-used electrode materials, in particular glassy carbon (GC), were not suitable for direct electron transfer in this configuration.

Heterologous expression of molybdenum-containing enzymes, especially members of the DMSO reductase family, is notoriously difficult. Recently, the dissimilatory arsenate reductase from *Shewanella* sp. str. ANA-3 was expressed in *Escherichia coli* but comparisons with the native enzyme were not made (Malasarn et al. (2008) J. Bacteriol. 190, 135-142). Expression was optimal when *E. coli* was grown anaerobically with DMSO although other electron acceptors for anaerobic growth were not tested and neither were different strains.

Since the entire native Aio is poorly expressed in a heterologous expression system, such as *E. coli*, use of this enzyme in routine detection of $As^{III}$ is not commercially viable.

As such, there is a need for improved methods and sensors for cheap and effective detection of $As^{III}$ in liquids such as drinking-water, waste-water and biological samples.

SUMMARY OF THE INVENTION

According to a first embodiment, the present invention provides an arsenite oxidase enzyme modified to prevent translocation to the periplasm, wherein the enzyme comprises the native AioA subunit from NT-26 and the native AioB subunit from NT-26, wherein a portion of the native AioB subunit corresponding to the translocation signal sequence, or a functional fragment thereof, is modified.

According to a second embodiment, the present invention is directed to the use of a modified $As^{III}$ oxidase according to the first aspect of the invention as a biosensor to detect the presence of $As^{III}$ in a sample.

According to a third embodiment, the present invention provides a microorganism, modified to express a heterologous $As^{III}$ oxidase according to the first aspect of the invention.

According to a fourth embodiment, the present invention provides a method of producing recombinant $As^{III}$ oxidase, comprising expressing the modified enzyme heterologously according to the first aspect of the invention in a microorganism.

According to a fifth embodiment, the present invention provides a device for detecting the presence of $As^{III}$ in a sample, comprising at least one electrode, an arsenite oxidase enzyme and a redox mediator.

DETAILED DESCRIPTION OF THE INVENTION

Figure 1:
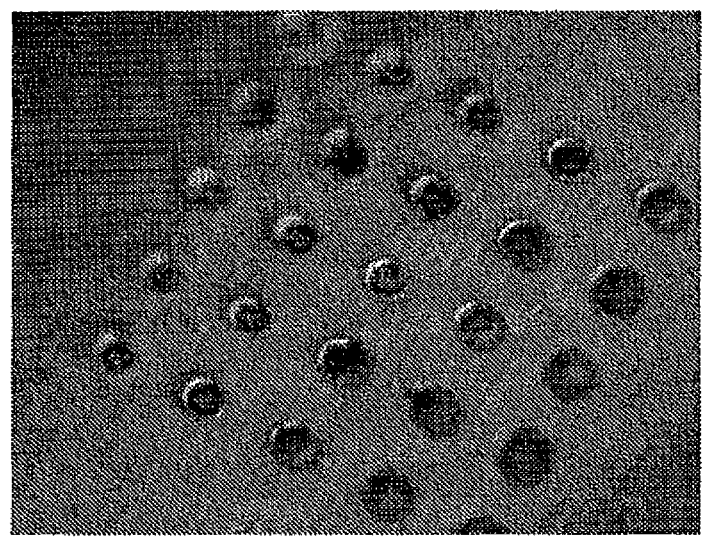
FIG. 1 shows the micro-structured surface of a device according to the invention.

The present inventors have developed a modified version of the native $As^{III}$ oxidase from Rhizobium sp. NT-26 (GenBank Accession Number AY345225) which can be successfully expressed in heterologous expression systems such as E. coli. This has been achieved by modifying a translocation signal sequence present in the native enzyme, or a functional fragment thereof, to prevent translocation.

The native $As^{III}$ oxidase consists of two heterologous subunits: AioB is the small subunit largely composed of beta sheets and AioA is the large subunit largely composed of alpha-helices (Santini & vanden Hoven (2004) J. Bacteriology. 186(6):1614-1619). The polypeptide sequence of wild-type AioB from Rhizobium sp. NT-26 is shown in SEQ ID No. 1 and SEQ ID No. 5 shows the corresponding nucleotide sequence. The AioB subunit comprises a Tat leader sequence (also referred to herein interchangeably as a Tat translocation signal sequence) which corresponds to the first 25 amino acids of SEQ ID No 1. This translocation signal sequence is shown as SEQ ID No. 2 and SEQ ID No. 6 shows the nucleotide sequence of the portion of the aioB gene encoding the translocation signal sequence. The signal sequence directs the transport of the protein to the periplasm using the Twin Arginine Translocation (Tat) pathway.

The present inventors have modified the native $As^{III}$ oxidase by modifying the translocation signal sequence in the AioB subunit. As a result of the modification, the modified enzyme is not exported from the host cytoplasm, and as a result can be expressed in large, commercially-viable quantities.

The translocation signal sequence can be modified by various methods which will be apparent to a person skilled in the art, including frame-shift mutations, substitution mutations or deletion. Any modification that results in loss of function of the native translocation signal sequence is within the scope of the invention, however deletion of the translocation signal sequence or a functional fragment thereof, is preferred.

Accordingly, a first aspect of the invention provides an $As^{III}$ oxidase modified to prevent translocation by modification of a translocation signal sequence, or a functional fragment thereof.

The modified $As^{III}$ oxidase comprises two subunits. The first subunit corresponds to the native AioA subunit from NT-26, or a variant, derivative or homologue thereof. The second subunit corresponds to the native AioB subunit from NT-26, or a variant, derivative or homologue thereof; however a portion of the native AioB subunit which corresponds to the translocation signal sequence, or a functional fragment of the translocation signal sequence, is modified in the enzyme of the invention. Preferably, the portion of the native AioB subunit which corresponds to the translocation signal sequence, or a functional fragment thereof, is modified by deletion.

In one embodiment, at least a portion of the aioB gene which encodes the translocation signal sequence, or a portion thereof encoding a functional fragment of the translocation signal sequence, is modified, preferably by deletion.

The portion of the aioB gene sequence encoding the translocation signal sequence is identified herein as SEQ ID NO. 6. Either the complete sequence identified as SEQ ID NO. 6 or a homologue of this sequence encoding a functional fragment of the translocation signal sequence may be modified according to the invention. As a result of the modification to the nucleotide sequence, the modified enzyme of the invention does not comprise the amino acid sequence identified herein as SEQ ID No. 2, or does not comprise a portion thereof that is required for a functional translocation signal sequence.

As used herein, the term 'functional fragment' means that the portion of the nucleotide sequence that is modified (e.g.

by deletion) encodes a polypeptide having Tat translocation signal sequence activity, preferably having at least the same activity of the polypeptide shown as SEQ ID NO: 2. As a result of the modification, the recombinant enzyme of the invention lacks such Tat translocation signal sequence activity.

As used herein, the term "homologue" refers to a nucleotide sequence that encodes a polypeptide which has Tat translocation signal sequence activity. With respect to sequence similarity, preferably there is at least 60%, more preferably at least 70%, more preferably at least 75%, more preferably at least 85%, more preferably at least 90% sequence similarity between SEQ ID NO. 6 and the sequence of the native aioB gene that is modified according to the invention. More preferably there is at least 95%, more preferably at least 98%, sequence similarity. These terms also encompass allelic variations of the sequences.

In another embodiment, the portion of the aioB gene that is modified according to the invention comprises or consists of the sequence identified herein as SEQ ID NO. 6.

SEQ ID No. 3 corresponds to the amino acid sequence of the AioB subunit excluding the entire native leader region. SEQ ID No. 7 shows the corresponding nucleotide sequence. If the entire AioB leader region is deleted, then the AioB subunit of the modified enzyme of the invention will correspond to SEQ ID No. 3. However, it is within the scope of the invention for a portion of the leader region within the AioB subunit to remain unmodified, provided that the portion of the leader region that is modified renders the remaining portion non-functional.

SEQ ID No. 4 shows the amino acid sequence of the AioA subunit and SEQ ID No. 8 shows the corresponding nucleotide sequence.

It is within the scope of the invention for the modified $As^{III}$ oxidase to comprise homologues, variants or derivatives of SEQ ID Nos. 3 and 4.

The terms "variant", "homologue", "derivative" or "fragment" as used herein include any substitution, variation, modification, replacement, deletion or addition of one (or more) amino acid from or to a sequence. The variant may have a deletion, insertion or substitution variation. The variation may produce a silent change and a functionally equivalent polypeptide, or may result in improved catalytic function or other characteristics of the resulting enzyme. Deliberate amino acid substitutions may be made on the basis of similar physio-chemical properties such as size, charge and hydrophobicity in order to alter the catalytic function or other properties or characteristics of the enzyme.

Unless the context admits otherwise, references to "AioA" and "AioB" include references to such variants, homologues and derivatives of the native subunits. The term "homologue" covers identity with respect to structure and/or function and is used to refer to peptides that share levels of sequence identity or similarity to SEQ ID Nos. 3 and 4 and retain at least the functionality of the native amino acid sequences. The variants may result in improvements in the catalytic activity or other properties of the resulting enzyme. These terms also encompass polypeptides derived from amino acids which are allelic variations of the aioA and/or aioB nucleic acid sequences (SEQ ID Nos. 7 and 8).

Levels of identity or similarity between amino acid sequences can be calculated using known methods. Publicly available computer based methods include BLASTP, BLASTN and FASTA (Atschul et al., Nucleic Acids Res., 25: 3389-3402 (1997)), the BLASTX program available from NCBI, and the GAP program from Genetics Computer Group, Madison Wis.

It is preferable if there is at least 60% sequence identity or similarity to the specified peptides of SEQ ID Nos. 3 and 4, preferably 70%, more preferably 80% and most preferably greater than 90%, e.g. at least 95% to the sequences of SEQ ID Nos. 3 and 4. The removal of the Tat leader sequence or a functional fragment thereof to prevent export to the periplasm is a known technique, and has been used previously in the production of heterodimeric molybdenum-containing enzymes (Malasarn et al. (2008), J Bacteriol, 190, 135-142). However, $As^{III}$ oxidase differs from other molybdenum-containing enzymes in that it is a much larger $\alpha_2\beta_2$ heterotetramer containing additional co-factors (i.e. a 3Fe-4S cluster and a Rieske 2Fe-2S cluster) not present in other molybdenum-containing enzymes). It has been demonstrated that the native enzyme is localised to the periplasm (Santini et al. (2000), J Bacteriol, 66, 92-97), given size of the assembled heterotetrameric complex it is therefore reasonable to speculate that two $\alpha\beta$ heterodimers formed in the cytoplasm are exported (via the Tat system) to the periplasm prior to heterotetrameric complex formation. Therefore, the present inventors were surprised to find that that following removal of the Tat leader sequence, the modified $As^{III}$ oxidase could achieve complete assembly (both subunit assembly and cofactor addition) to form a heterotetramer in the cytoplasm of the various E. coli strains.

For the avoidance of doubt, the abbreviations "aio", "Aio", "aro", "Aro", "aso" and "Aso" can be used interchangeably and all refer to the arsenite oxidase enzyme (gene or protein). The different abbreviations are the result of different nomenclature that has been used in the art (Lett et al., J. Bacteriology, 4 Nov. 2011; p. 207-208).

The advantage of modifying the native $As^{III}$ oxidase according to the invention is that is can be expressed successfully in heterologous expression systems such as E. coli at high, commercially-viable yields. Once expressed, the enzyme can be used to detect the presence of $As^{III}$. Therefore, a second aspect of the invention is directed to the use of the modified arsenite oxidase enzyme according to the first aspect of the invention as a biosensor to detect the presence of $As^{III}$ in a sample. The modified enzyme of the invention has been found to be equally effective as the native enzyme in catalysing the oxidation of $As^{III}$ to arsenate $As^V$ (Warelow & Santini, unpublished data). The absence of the translocation sequence does not impact upon the catalytic activity of the enzyme. The modified enzyme is therefore suitable for use in biosensors to detect the presence of $As^{III}$.

Preferably the sample is a liquid sample. The liquid sample may be any type of liquid that is susceptible to $As^{III}$ contamination, including, but not limited to, ground-water, drinking-water, environmental liquids such as mining effluent and sewage, waste-water, biological samples.

Preferably the modified enzyme of the invention may be used in laboratory-based biosensors or, preferably, in low-cost disposable biosensor suitable for field use (i.e. detecting $As^{III}$ in a sample at the source of the sample rather than in a laboratory).

The advantage of utilising the modified enzyme according to the first aspect of the invention in a biosensor for detecting $As^{III}$ in a sample is that it can be expressed in commercially-viable quantities in a variety of heterologous expression systems, including, unexpectedly, host strains that are normally used for cloning rather than protein expression.

Therefore, according to a third aspect the present invention provides a microorganism modified to express the heterologous $As^{III}$ oxidase of the first aspect of the invention. The wild-type microorganism may be selected from a range of species including, but not limited to, E. coli. Preferably, the wild-type microorganism is *E. coli*, in particular *E. coli* K12 strains DH5α and JM109λpir.

It is surprising that these strains have been found to be the most suitable for expressing the recombinant enzyme of the invention, since they are usually used in the art for cloning, rather than protein expression. As detailed in Example 1 below, the inventors found that unexpectedly high yields were achieved using *E. coli* strains DH5α and JM109λpir rather than strains BL21 (protease-deficient) and Origami, which are commonly used for heterologous expression of recombinant enzymes.

*E. coli* strain DH5α is a Hoffman-Berling 1100 strain derivative and can be purchased from Invitrogen™. The properties of this strain are described by the following standard nomenclature:

F-endA1 glnV44 thi-1 recA1 relA1 gyrA96 deoR nupG Φ80dlacZΔM15 Δ(lacZYA-argF)U169, hsdR17(rK–mK+), λ–.

The DH5α strain is described in the following publications: FOCUS (1986) 8:2, 9.; Hanahan, D. (1985) in DNA Cloning: A Practical Approach (Glover, D. M., ed.), Vol. 1, p. 109, IRL Press; Grant, S. G. N. et al. (1990) Proc. Natl. Acad. Sci. USA 87: 4645-4649 PMID 2162051; and Meselson M. and Yuan R. (1968) Nature 217:1110 PMID. 4868368.

*E. coli* strain JM109λpir can be purchased from Promega and has the following standard nomenclature properties:
endA1 glnV44 thi-1 relA1 gyrA96 recA1 mcrB+ Δ(lac-proAB) e14– [F' traD36 proAB+ lacIq lacZΔM15] hsdR17 (rK–mK+).

This strain is described in Yanisch-Perron et al (1985) Gene, 33(1):103-19; and Penfold et al (1992) Gene 118: 145-146.

According to a fourth embodiment, the present invention provides a method of producing recombinant $As^{III}$ oxidase, comprising expressing the modified enzyme according to the first aspect of the invention in a heterologous microorganism. According to an embodiment of this aspect of the invention, novel primers identified herein as SEQ ID NO. 9 and SEQ ID NO. 10 can be used to clone the NT-26 aioB and aioA genes (termed aioBA) into the commercially-available pPROEX Htb vector (Invitrogen). As described in relation to the first aspect of the invention, the aioB gene is modified to delete at least the portion of the nucleotide sequence (SEQ ID NO. 6) encoding at least the functional portion of the TAT leader sequence shown herein as SEQ ID NO. 2.

Preferably the heterologous microorganism is *E. coli*, and preferably *E. coli* strains DH5α or JM109λpir. The present inventors have found that strain DH5α provides optimal expression of the heterologous arsenite oxidase enzyme when grown aerobically and JM109λpir provides optimal expression of the heterologous enzyme when grown anaerobically with nitrate as the electron acceptor. Furthermore the inventors have found that use of an affinity tag at the N-terminus of AioB allows for simple purification. This embodiment is described in more detail in Example 1 below.

According to a fifth aspect, the present invention provides a device for detecting the presence of $As^{III}$ in a sample. The device comprises an electrode (termed the "test electrode") incorporating an $As^{III}$ oxidase enzyme and a redox mediator.

The device may comprise wild-type $As^{III}$ oxidase or the modified $As^{III}$ oxidase according to the first aspect of the present invention. Preferably, the enzyme is the modified $As^{III}$ oxidase. As discussed above, high yields of the modified enzyme can be obtained through heterologous expression in *E. coli*. Therefore, it is preferable to use the modified enzyme to keep the manufacturing cost of the device low and to enable the device to be manufactured in commercially-viable quantities.

In one embodiment, the device comprises a test strip made of polymer or ceramic materials. Preferably, the device comprises two or more planar electrodes. Preferably the device comprises a "reference electrode" in addition to the test electrode. At least the test electrode incorporates the $As^{III}$ oxidase.

The device includes a redox mediator. The term "redox mediator" is defined as any moiety capable of transferring electrons from the enzyme to the electrode surface. Artificial redox mediators such as 2,6-dichlorophenolindophenol (DCPIP) are often used in solution in laboratory-based spectrophotometric measurements; however spectrophotometric measurements are not routinely used in field test equipment. The inclusion of a redox mediator is advantageous in a number of different ways, compared with existing devices in which the enzyme is directly linked to an electrode. The presence of a redox mediator improves the efficiency of electron transfer and reduces the effects of electrode surface chemistry on the currents measured. This enables a much wider range of electrode materials to be used. As the background currents due to sample components are dependent on the electrode material this gives greater versatility in optimising signal to background.

As shown in Example 2, a wide range of mediators can be used in the in the electrochemical $As^{III}$-sensing device of the invention. Examples of suitable redox mediators include, but are not limited to, metal complexes where the metal exists in two or more different redox states, for example iron, ruthenium or osmium complexes, organic molecules that can exist in two or more accessible redox states, for example cytochromes, conducting organic polymers, conducting organic salts, 2,6-dichlorophenolindophenol, ferrocene and ferrocene derivates including ferrocene carboxylic acid and hydroxymethyl ferrocene (ferrocene methanol), Tris(2,2'-bipyridine)dichlororuthenium(II), tetrathiafulvalene (TTF) and quinones including, but not limited to, benzoquinone and hydroquinone. However not all redox mediators are effective with Aio (arsenite oxidase), for example tetraamine ruthenium (III) chloride, methylene blue, ferricyanide and oxygen have been found not to be effective.

Advantageously, the device of the invention is versatile and has been shown to work with a variety of test electrode materials (see Example 2 below). Preferably, the test electrode is made of one or more conducting materials including, but not limited to, carbon, carbon nanotubes, graphene, graphite, gold, platinum, palladium, glassy carbon, nanostructured metal oxides or nanostructured metal.

Preferably, the reference electrode comprises a reference redox couple, such as Ag/AgCl.

The electrode materials can be deposited on the test strip by a variety methods including, but not limited to, screen-printing or evaporation. The electrodes may be open or covered by a lid so forming a defined volume cell. There may, or may not, be a membrane covering the electrodes.

The test strip is suitable for laboratory use and, preferably, field-based use (i.e. $As^{III}$ can be detected in a sample at the source using the test strip or device). The device may be suitable for multiple uses or a single use, and may be disposable.

Preferably, the device comprises a micro-structured surface, with the enzyme entrapped thereon with a mediator (see FIG. 1). A micro-structured surface, for example pillars rising from the base of the electrode, improves the performance of the electrode.

Preferably the sample in which $As^{III}$ is detected using the device of the invention is a liquid sample. The liquid sample may be any type of liquid that is susceptible to $As^{III}$ contamination, including, but not limited to, ground-water, drinking-water, environmental liquids such as mining effluent and sewage, waste-water, biological samples.

Figure 2:
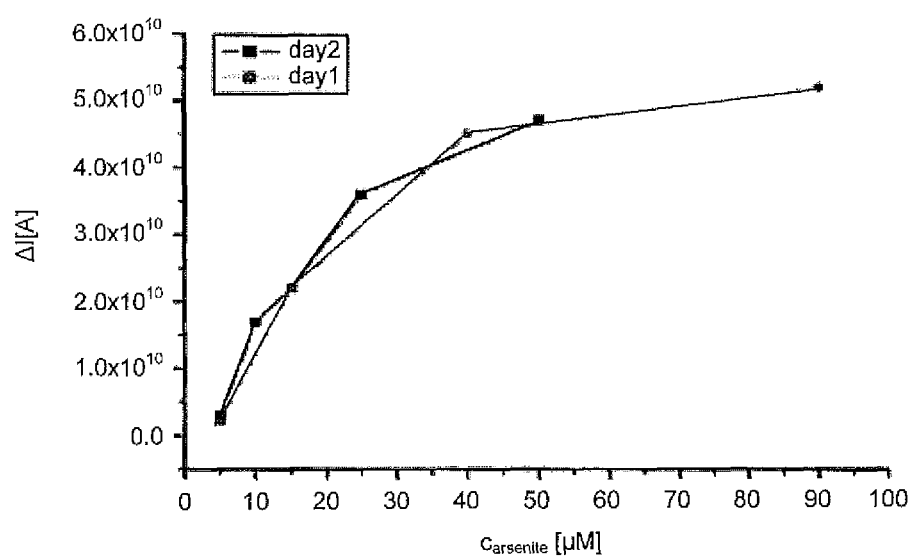
FIG. 2 is an $As^{III}$ dose-response curve showing the comparable results of the sensor of the invention over two consecutive days.

In use, the test sample is brought into direct contact with the test strip. Operation of the sensor device involves applying an electrical potential between the test and reference electrodes and measuring the current. A number of methods would be apparent to those skilled in the art, and include, but are not limited to, chronoamperomerty, square wave voltammetry and coulometry. The response to $As^{III}$ can be measured from 5 µM to 40 µM with the same sensor showing comparable results the next day (see FIG. 2).

The advantages of using the device of the invention as described above to test for the presence of $As^{III}$ in a sample are that the sensitivity for the analyte is high and the test is specific for $As^{III}$ (i.e. the most toxic soluble form of arsenic) due to the presence of the enzyme; the test is quick and results are obtained almost instantaneously; the device is simple to use; the results are reproducible; and the device can be produced and purchased cheaply (particularly important for use in developing countries).

The present invention is further described with reference to the following examples.

EXAMPLE 1

Experimental Procedures
Bacterial Strains, Plasmid and Growth Conditions

*Escherichia coli* strains DH5α, JM109λpir, RK4353, C43, BL21 and Origami were used to test expression of the NT-26 arsenite oxidase. The expression vector pPROEX-HTb (Invitrogen) was used for expression purposes. All expression conditions involved growing *E. coli* in LB containing 100 µg/ml ampicillin either aerobically (with aeration at 170 rpm (1:5 ratio liquid to head space) or anaerobically with nitrate (14 mM) or DMSO (14 mM) as electron acceptors and sodium lactate (20 mM) as the electron donor.
Cloning and Expression The NT-26 aioB and aioA (aioBA) genes were amplified without the native Tat leader sequence using the following primers:

```
Forward:
PROEXAroBFHis
                                       (SEQ ID No. 9)
5'-GCGAATTCAAGCTACCGCGGCGGCAGGGGTC-3'

Reverse:
PROEXAroAR
                                      (SEQ ID No. 10)
5'-GCCTGCAGTCAAGCCGACTGGTATTCTTTCGA-3'
```

The restriction enzymes EcoRI and PstI (underlined above) were used to facilitate cloning into the expression vector, pPROEX-HTb. The pPROEX-HTb carrying the aioBA genes was transformed into a variety of *E. coli* strains to determine which one gave optimal expression. A variety of IPTG (Isopropyl β-D-1-thiogalactopyranoside) and sodium molybdate (Mo) concentrations as well as time of induction were tested. The final optimum expression conditions used for purification of the Aio involved growing DH5α aerobically at 21° C. for 24 hrs in LB containing 40 µM IPTG and 1 mM Mo.

Purification of Recombinant Arsenite Oxidase

Recombinant Aio was purified from DH5α using a combination of affinity and size exclusion chromatography. Cells were harvested by centrifugation at 9,700×g for 10 minutes. The cell pellets were pooled and washed by suspending in binding buffer (10 ml/gm wet weight cells) (20 mM potassium phosphate, 500 mM sodium chloride, 20 mM imidazole, pH 7.2) and centrifuged at 12,000×g for 15 minutes. The cell pellet was then re-suspended in binding buffer (10 ml/gm wet weight cells). The *E. coli* cells were disrupted by a single pass through a French pressure cell (12,000 psi) and the cell debris removed by centrifugation at 30,000×g for 30 minutes. The supernatant was loaded onto a GraviTrap pre-packed Ni charged affinity chromatography column (GE Healthcare) as per the manufacturer's instructions except with one minor modification; the wash volume used was 120 ml. The eluent was desalted in 50 mM 2-(N-morpholino) ethanesulfonic acid (MES) (pH 5.5) buffer resulting in the precipitation of non-target co-eluted protein(s) which were removed by centrifugation at 10,000×g for 5 minutes. The supernatant was filtered through a 0.22 µm filter (Millipore), concentrated using a Vivaspin 20 (MWCO 100,000) (GE Healthcare) centrifugal concentrator and loaded onto a Superdex 200 gel filtration column (GE Healthcare) pre-equilibrated with 50 mM MES, 100 mM NaCl, pH 5.5 buffer. Chromatography was carried out at a flow rate of 0.3 ml/min. The 0.25 ml fractions containing Aio activity were pooled and concentrated using a Vivaspin 20 centrifugal concentrator (MWCO 100,000).

Confirmation of the native molecular mass of the recombinant Aio was done using a Superdex 200 gel filtration (GE Healthcare) chromatography column. A calibration curve was created using a gel filtration calibration kit (GE Healthcare) of known molecular mass proteins (Thyroglobulin 669 kDa, Ferritin 440 kDa, Aldolase 158 kDa, Conalbumin 75 kDa, Ovalbumin 43 kDa) and the void volume of the column was determined using Blue dextran 2000 (2,000 kDa). Chromatography conditions used were as per the manufacturers' instructions with a flow rate of 0.3 ml/min.
Results and Discussion
Heterologous Expression and Purification of the Recombinant Arsenite Oxidase In this study the aioB and aioA (designated aioBA) genes were cloned without the aioB Tat leader sequence allowing for expression in the *E. coli* cytoplasm. A combination of different strains and growth conditions were tested to optimise Aio expression. Surprisingly, the highest Aio specific activity was obtained with *E. coli* K12 strains DH5α and JM109λpir.

Figure 3:
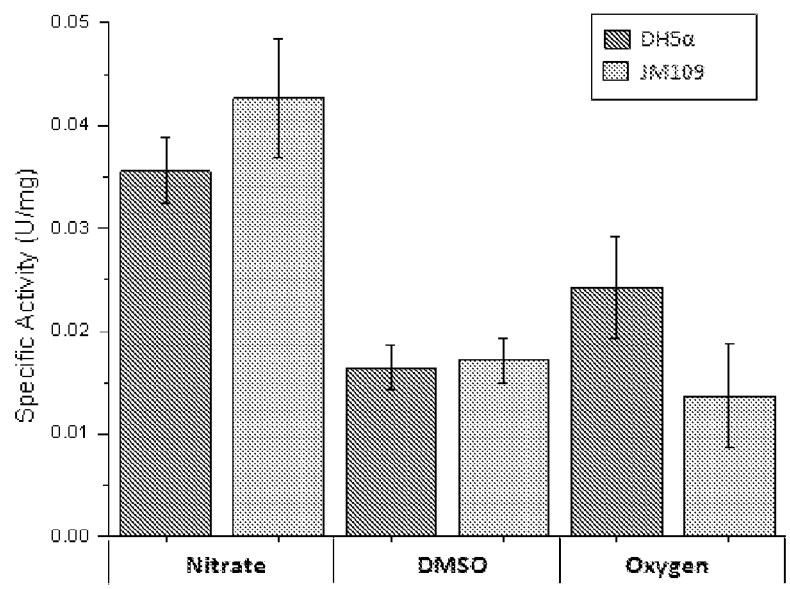
FIG. 3 is a comparison of $As^{III}$ oxidase activities in total cell extracts of E. coli strains DH5α and JM109λpir grown with different electron acceptors.
Figure 4:
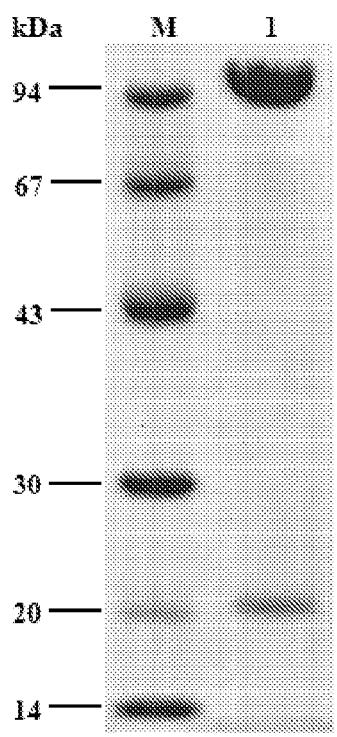
FIG. 4 shows a SDS-Polyacrylamide gel (12%) of purified recombinant NT-26 $As^{III}$ oxidase (M: Molecular weight marker: phosphorylase b (94 kDa), albumin (67 kDa), oval albumin (43 kDa), carbonic anhydrase (30 kDa), trypsin inhibitor (20 kDa), β-lactalbumin (14 kDa) (GE Healthcare) 1: Purified recombinant AioBA, two subunits AioA (~94 kDa) AioB with N-terminal His-tag (~19 kDa))
Figure 5A:
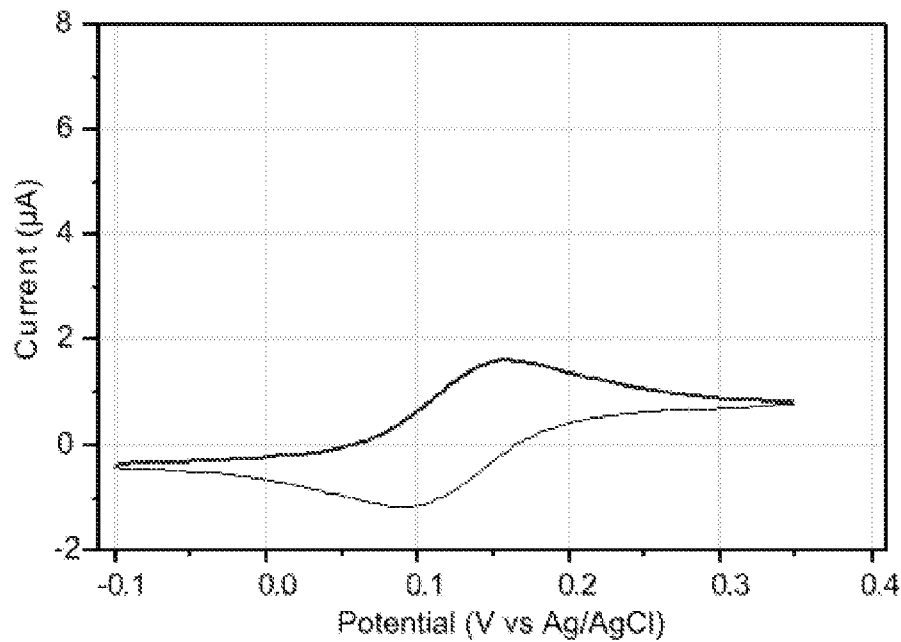
FIGS. 5 (a-j) show cyclic voltammogram measurements and chrono amperometry for a device according to the invention including ferrocene methanol as the mediator.
Figure 5B:
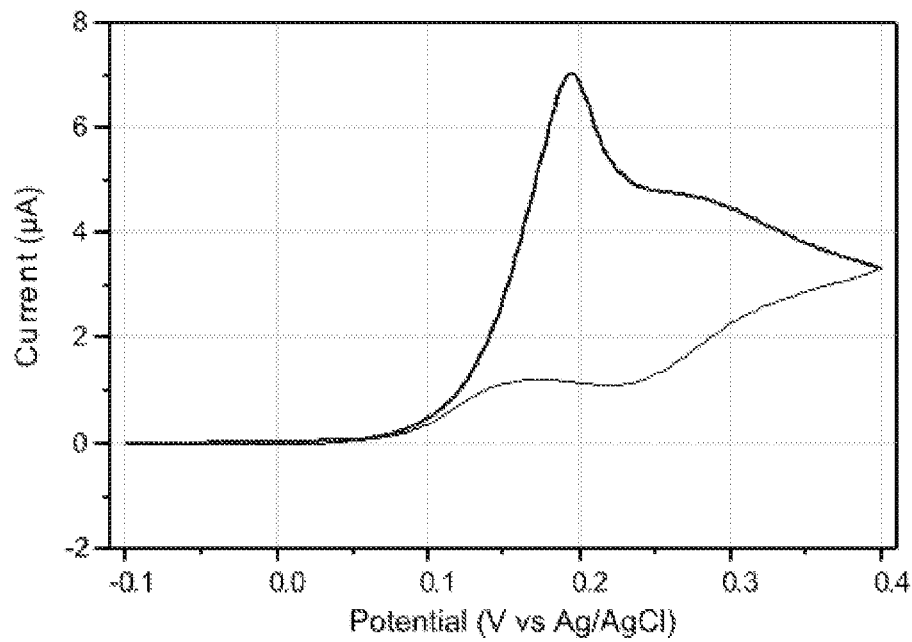
Figure 5C:
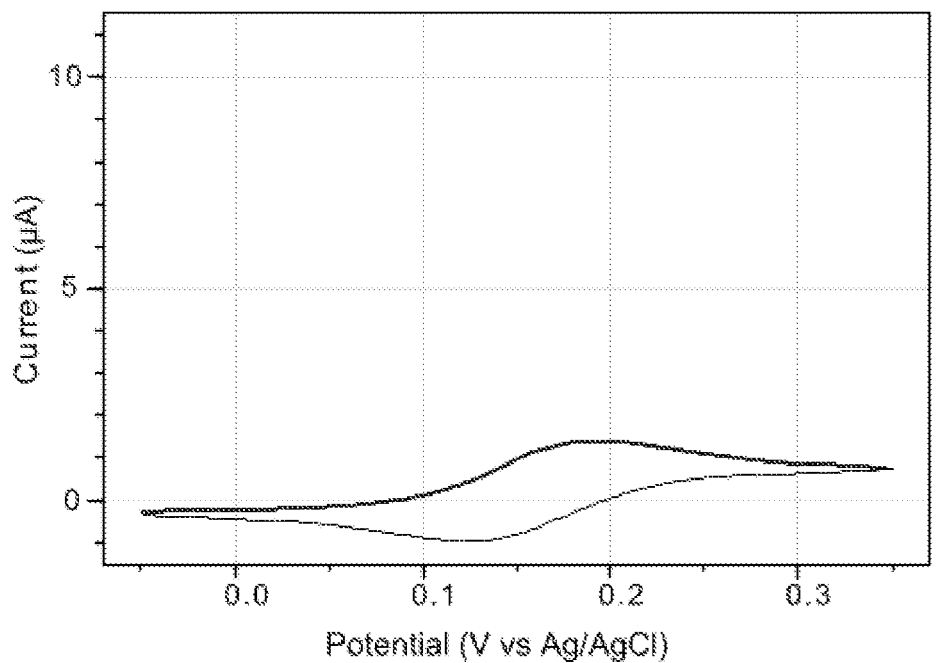
Figure 5D:
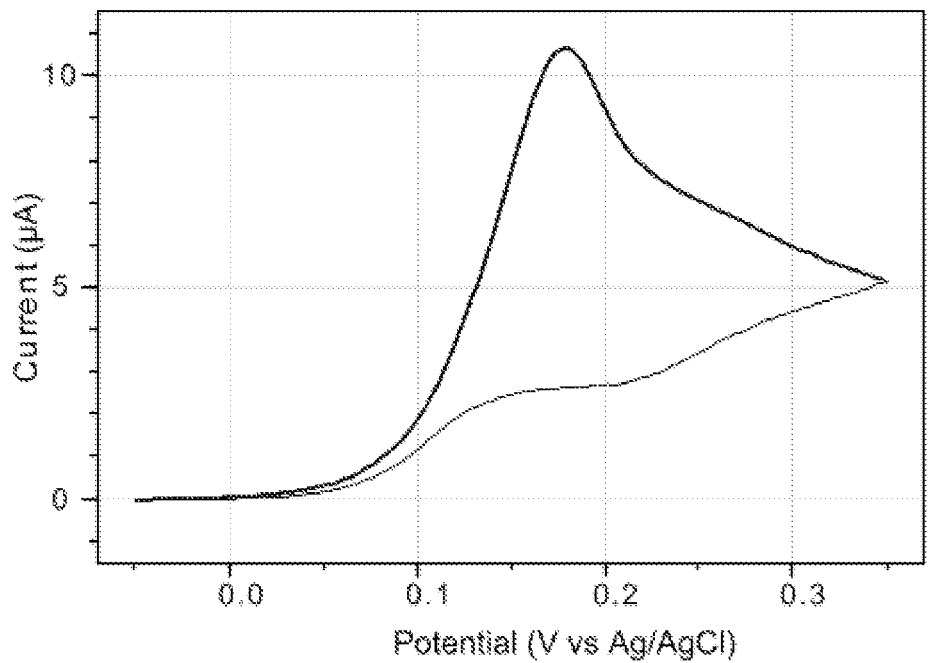
Figure 5E:
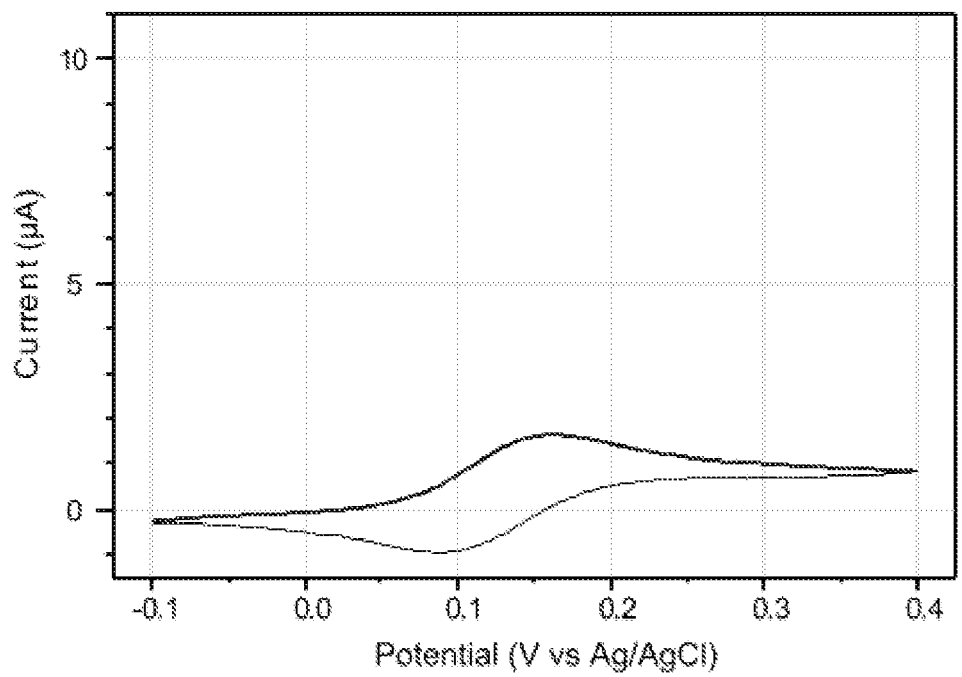
Figure 5F:
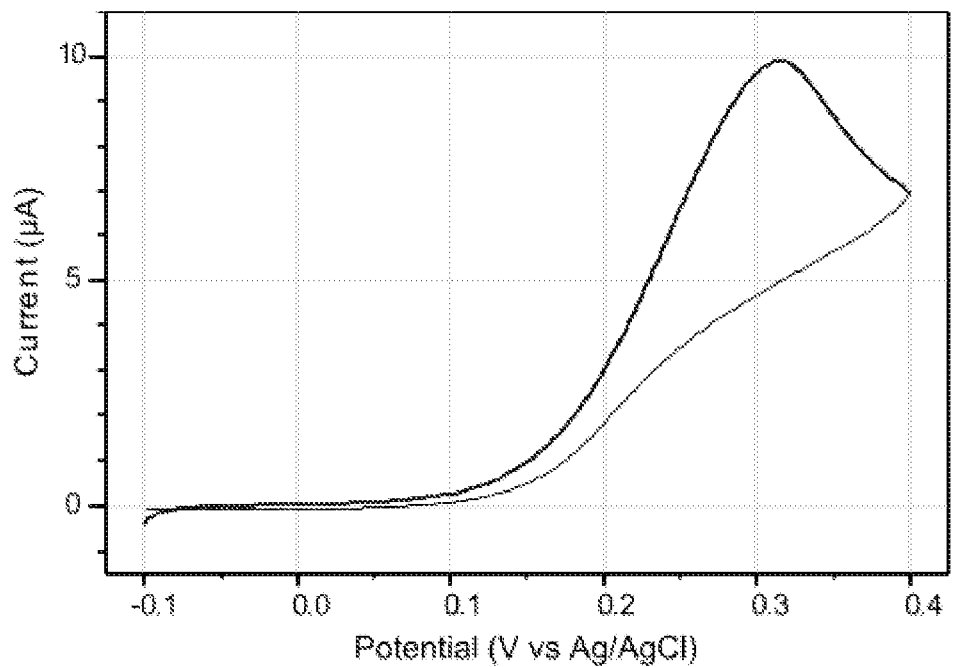
Figure 5G:
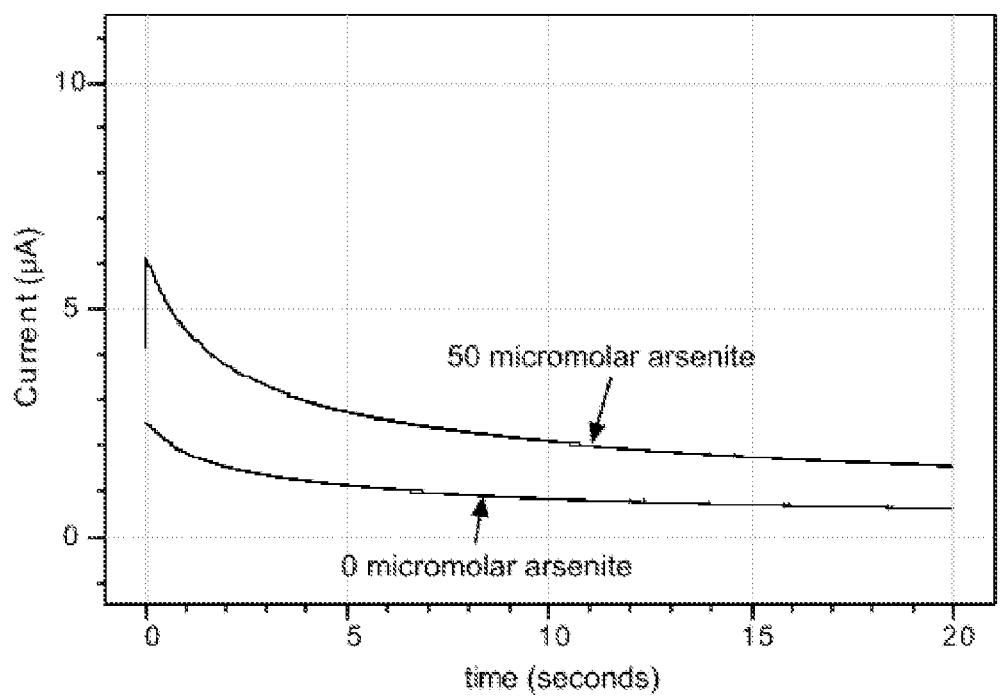
Figure 5H:
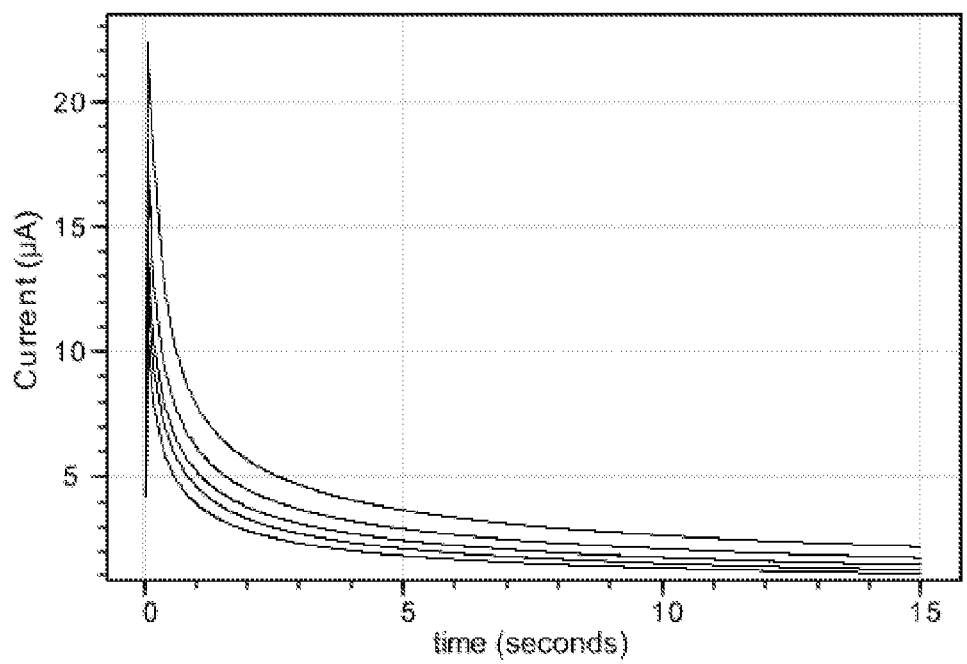
Figure 5I:
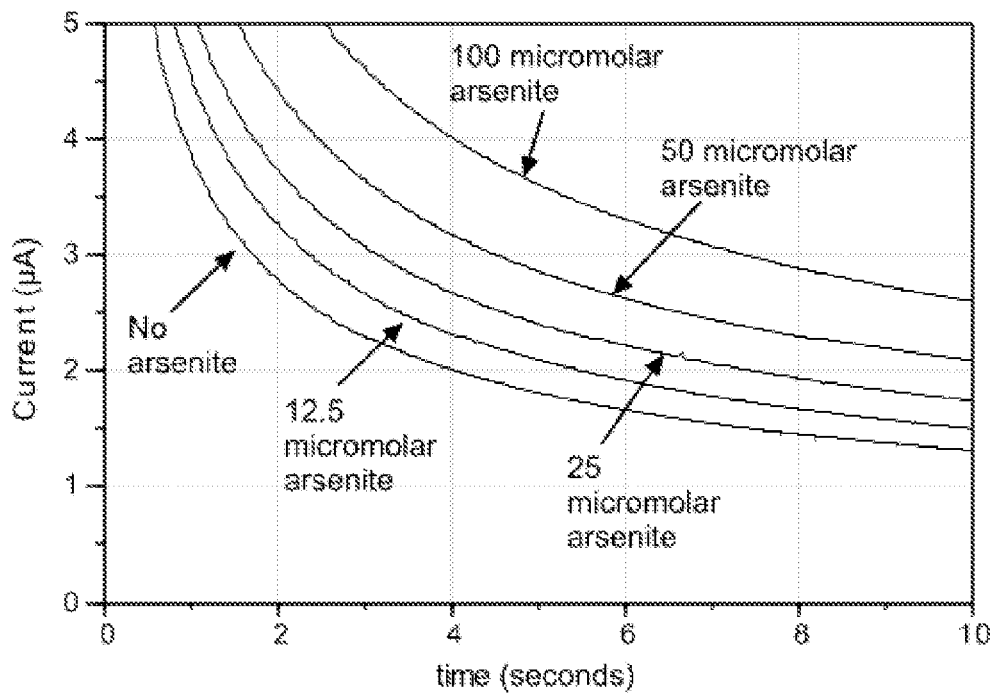
Figure 5J:
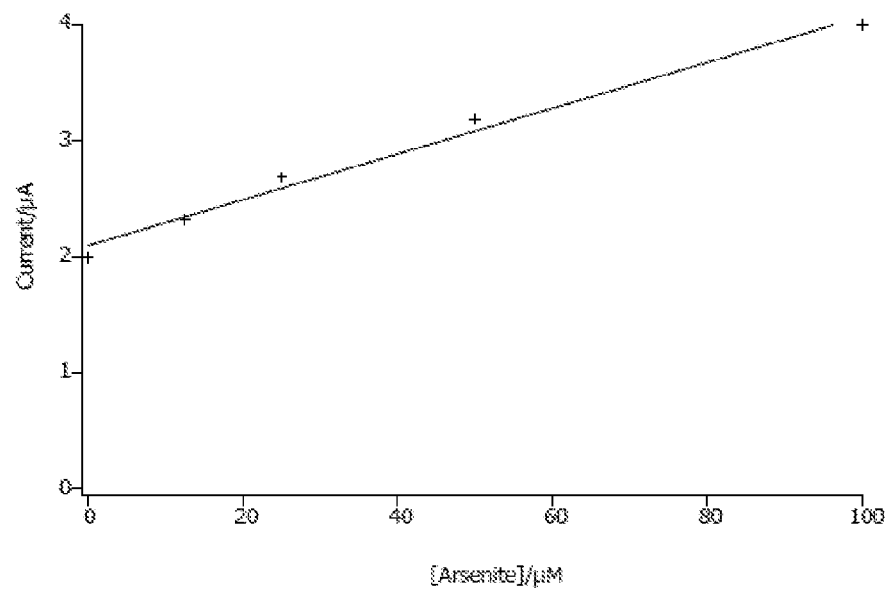
Figure 6A:
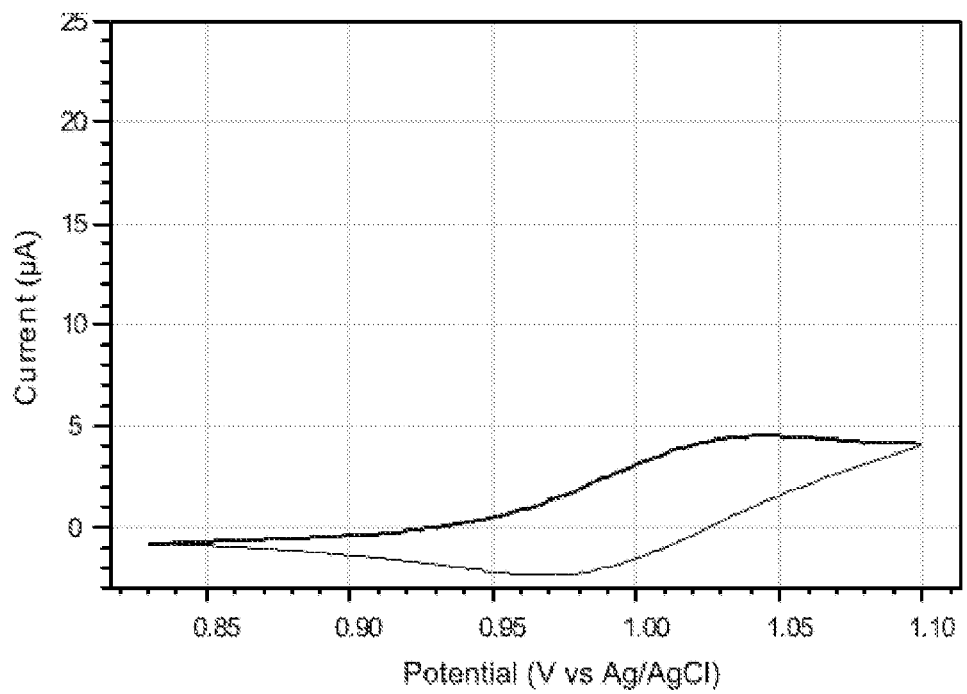
FIGS. 6 (a-d) shows show cyclic voltammogram measurements for a device according to the invention including Tris(2,2'-bipyridine) dichlororuthenium(II) as the redox mediator.
Figure 6B:
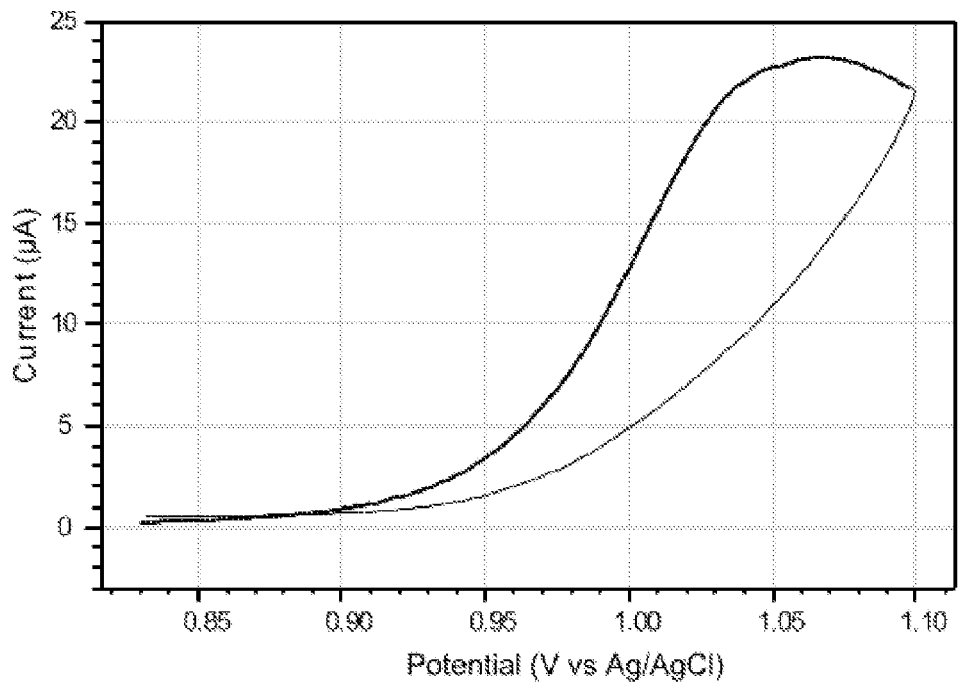
Figure 6C:
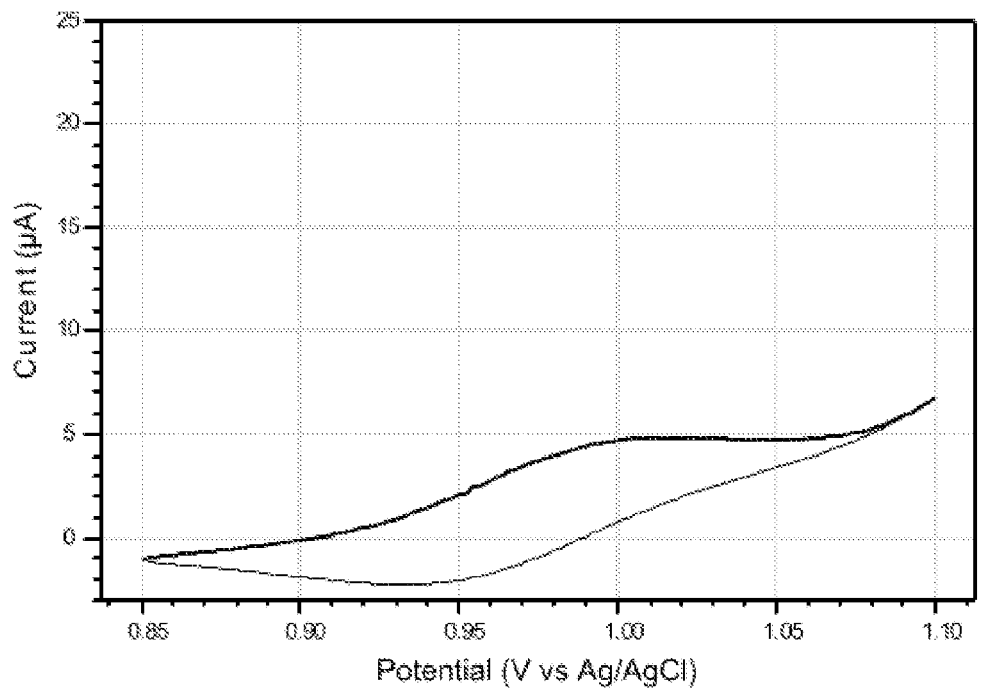
Figure 6D:
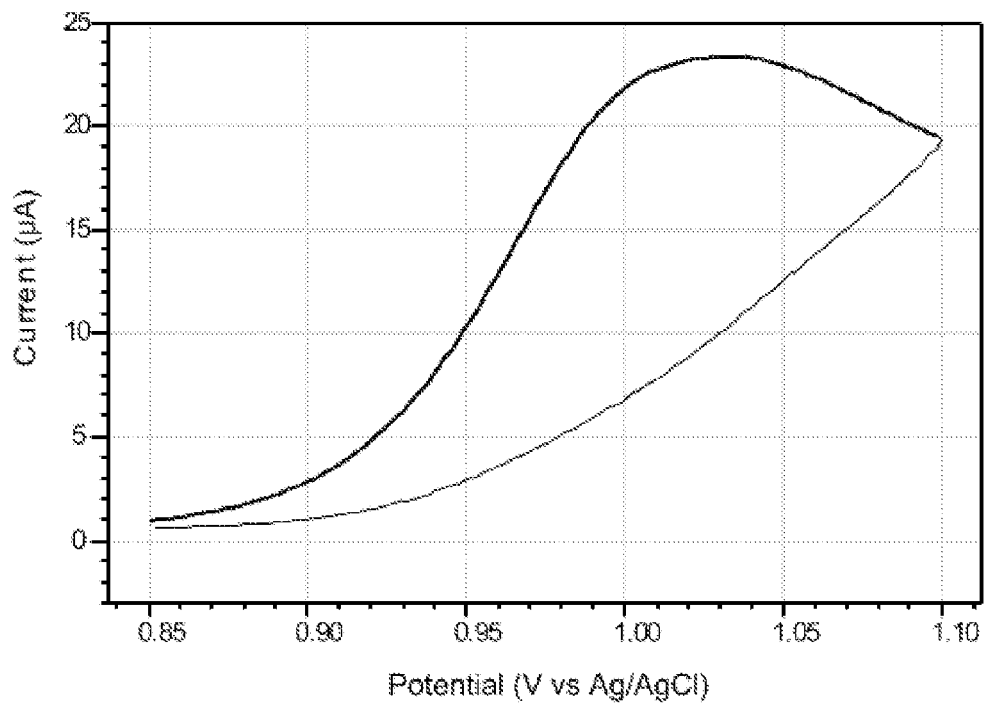

Interestingly, there was also a variation of Aio activity when different electron acceptors were used (FIG. 3), with nitrate the optimal electron acceptor. Given the greater cell yield obtained from aerobic growth, DH5α and oxic conditions were chosen for further studies. Recombinant $As^{III}$ oxidase was purified from *E. coli* using a combination of Ni-NTA and size exclusion chromatography. Based on SDS polyacrylamide gel electrophoresis, the recombinant enzyme was >99% pure and contained the two known Aio subunits, AioA (93 kDa) and AioB (21 kDa) (see FIG. 4). Based on size exclusion chromatography the native molecular mass of the enzyme was 219 kDa which is consistent with the $\alpha_2\beta_2$ oligomeric state of the native enzyme purified from NT-26 (Santini & vanden Hoven, 2004, J. Bacteriology. 186(6):1614-1619).

EXAMPLE 2

A number of experiments were performed to demonstrate that the enzyme described within the patent application can be used in an enzyme mediated electrochemical device to detect arsenite in water. The results demonstrate that a range of redox mediator molecules can be used in the device and that the electrode material can also be varied.

Materials & Methods

Screen printed electrodes were purchased from Dropsens (Oviedo, Spain). Carbon screen printed electrodes have a carbon working electrode (4 mm diameter) and counter electrode and silver/silver chloride reference electrode (product ref. DRP-C110). Carbon nanotube screen printed electrodes have a multi-walled carbon nanotube working electrode (4 mm diameter), carbon counter electrode and silver/silver chloride reference electrode (produce reference DRP-110CNT). Gold screen printed electrode have a gold working electrode (4 mm diameter) and counter electrode and a silver/silver chloride reference electrode (product reference DRP-220AT). Electrochemical measurements (cyclic voltammetry and chrono amperometry) were recorded using a CompactStat.e potentiostat instrument (Ivium Technologies) and IviumSoft software (Ivium Technologies). 2,6-dichlorophenolindophenol, Ferrocene Carboxylic acid, hydroxymethyl ferrocene (ferrocene methanol), tetrathiafulvalene (TTF) and Tris(2,2'-bipyridine)dichlororuthenium(II) mediators were all purchased from Sigma Aldrich. 50 mM solution of sodium arsenite (Fluka) was also purchased from Sigma Aldrich.

In all experiments the working, counter and reference electrodes were completely covered with a 200 µl buffered solution containing the required amount of mediator, arsenite oxidase enzyme and arsenite for each experiment.

Cyclic voltammograms were recorded using carbon, carbon nanotube and gold electrodes with a 0.5 mM hydroxymethyl ferrocene solution (10 mM PBS, pH 7.1, 100 mM KCl) containing 0.05 U arsenite oxidase (0.17 nanomoles) with and without 500 micromolar sodium arsenite. A scan rate of 5 mV/s was used. Chrono amperometry was performed using a 0.25 mM hydroxymethyl ferrocene solution (10 mM PBS, pH 7.1, 100 mM KCl) containing 0.05 U arsenite oxidase (0.17 nanomoles) with 0 and 50 micromolar sodium arsenite when using a carbon electrode and 0, 12.5, 25, 50 and 100 micromolar sodium arsenite when using a gold electrode. The solution was mixed between each chrono amperometry run. Triplicate runs were recorded for each concentration of arsenite and the average values plotted. A one step potential of 0.35 V (vs Ag/AgCl) was applied for each run.

Cyclic voltammograms were recorded using carbon and carbon nanotube electrodes with a 1 mM Tris(2,2'-bipyridine)dichlororuthenium(II) solution (10 mM PBS, pH 7.1, 100 mM KCl) containing 0.05 U arsenite oxidase (0.17 nanomoles) with and without 500 micromolar sodium arsenite. A scan rate of 5 mV/s was used.

Cyclic voltammograms were recorded using carbon and gold electrodes with a 1 mM ferrocene carboxylic acid solution (10 mM PBS, pH 7.1, 100 mM KCl) containing 0.1 U arsenite oxidase (0.34 nanomoles) with and without 1 mM sodium arsenite. A scan rate of 5 mV/s was used. Chrono amperometry was performed using a 1 mM ferrocene carboxylic acid solution (10 mM PBS, pH 7.1, 100 mM KCl) containing 0.1 U arsenite oxidase (0.34 nanomoles) with 0, 50 and 100 micromolar sodium arsenite with a carbon electrode. A single step run was performed applying a potential of 0.38 V (vs Ag/AgCl reference electrode). The solution was mixed between each chrono amperometry run. Duplicate runs were recorded for each concentration of arsenite.

Cyclic voltammograms were recorded using carbon, carbon nanotube and gold electrodes with a 1 mM 2,6-dichlorophenolindophenol (DCPIP) solution (50 mM MES, pH 5.5, 100 mM KCl) containing 0.05 U arsenite oxidase (0.17 nanomoles) with and without 500 micromolar sodium arsenite. A scan rate of 5 mV/s was used.

Cyclic voltammograms were recorded using carbon nanotube electrode by first depositing 6 µl of 2 mM tetrathiafulvalene (TTF) in acetone onto the working electrode and allowing to dry for 10 minutes. The electrode screen printed electrode was then immersed in 200 µl solution (10 mM PBS, pH 7.1, 100 mM KCl) containing 0.05 U arsenite oxidase (0.17 nanomoles) with and without 500 micromolar sodium arsenite. A scan rate of 50 mV/s was used.

Results 2,6-dichlorophenolindophenol, Ferrocene Carboxylic acid, Ferrocene Methanol and Tris(2,2'-bipyridine)dichlororuthenium(II) mediators all showed reversible redox behaviour in the presence of the enzyme (very similar cathodic and anodic peak currents) and an increased cathodic peak current relative to the anodic peak current in the presence of the enzyme and arsenite. This is a typical response of an enzyme mediated electrochemical device.

FIGS. 5 (a-f) show cyclic voltammograms of ferrocene methanol as the mediator with carbon (a and b), carbon nanotube (c and d) and gold (e and f) screen printed electrodes without (a, c, e) and with 500 micromolar arsenite (b,d,f). FIG. 5g shows chronoamperometry plots of ferrocene methanol plus enzyme, and ferrocene methanol plus enzyme plus 50 µM arsenite recorded using a carbon electrode. FIGS. 5h and 5i show chronoamperometry plots of ferrocene methanol plus enzyme, and ferrocene methanol plus enzyme plus 0, 12.5, 25, 50 and 100 micromolar arsenite recorded using a gold electrode. FIG. 5i is a zoomed portion of FIG. 5h. FIG. 5j is a plot showing a linear dose response of current to arsenite concentration and refers to the Chrono amperometry plots in FIGS. 5h and 5i, plotting current values taken at four seconds from the chrono amperometry plots.

FIGS. 6 (a-d) show cyclic voltammograms of Tris(2,2'-bipyridine) dichlororuthenium(II) as the mediator with carbon (a and b) and carbon nanotube (c and d) screen printed electrodes, without (a and c) and with (b and d) 500 micromolar arsenite.

Figure 7A:
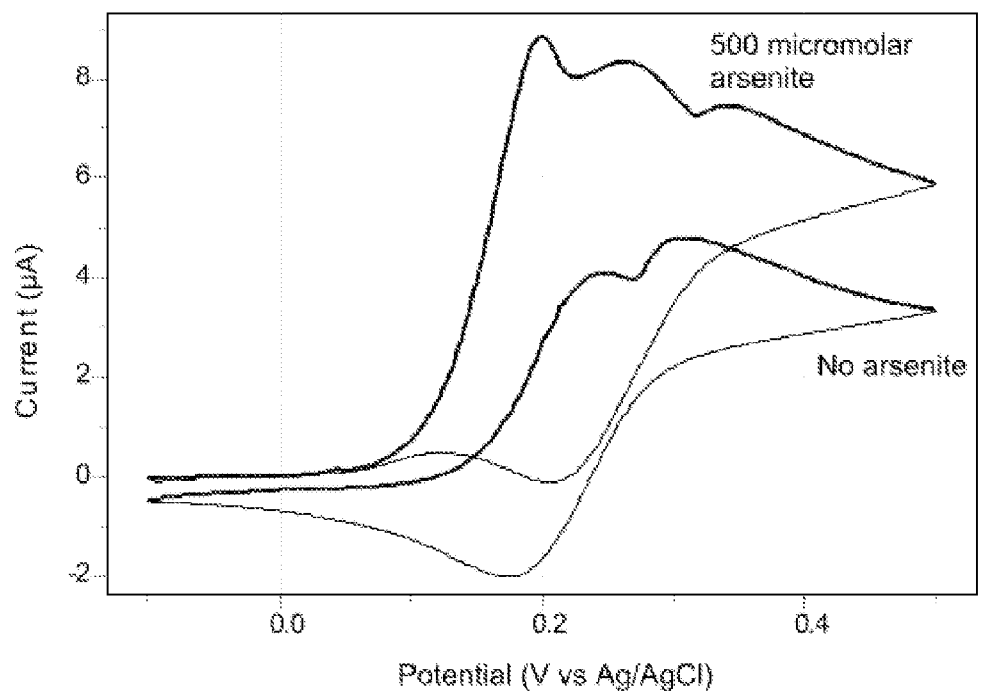
FIGS. 7a, 7b and 7c show cyclic voltammogram and chrono amperometry measurements for a device according to the invention including feccocene carboxylic acid as the mediator.
Figure 7B:
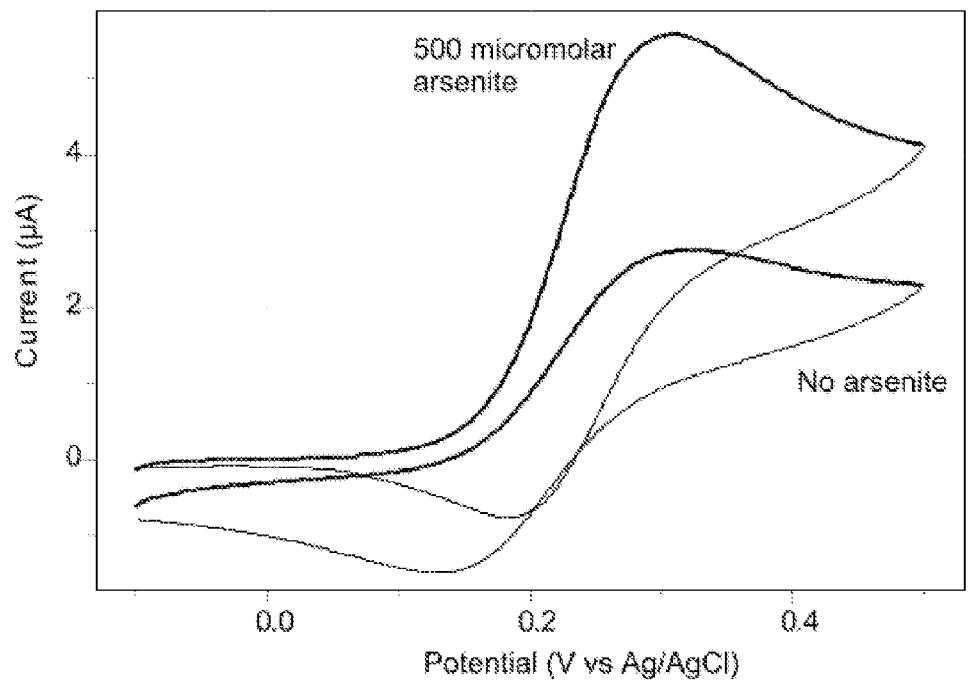
Figure 7C:
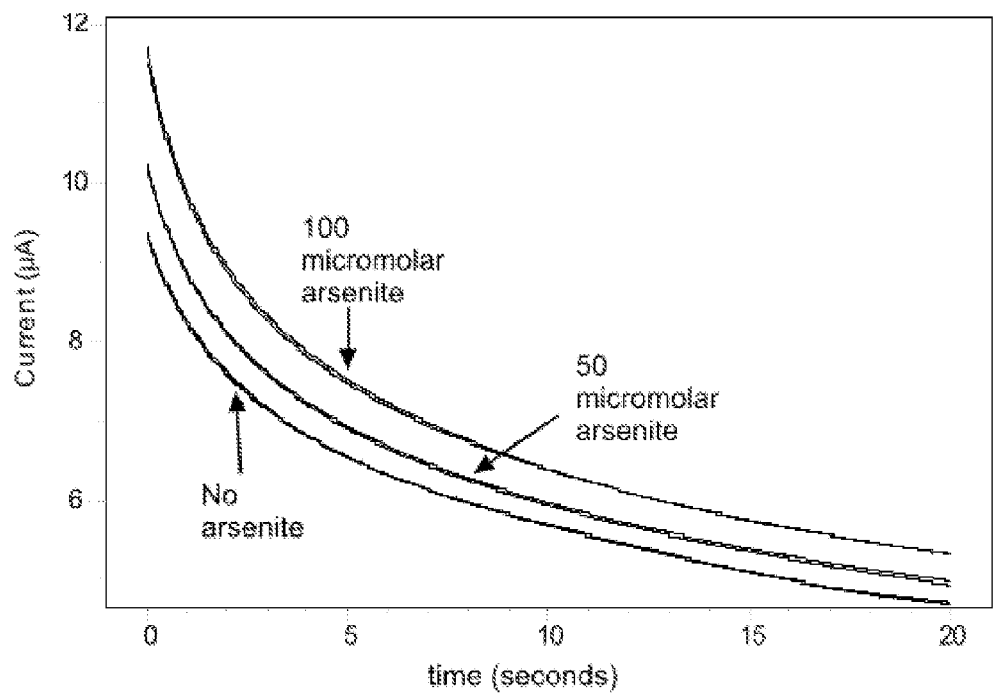
Figure 8A:
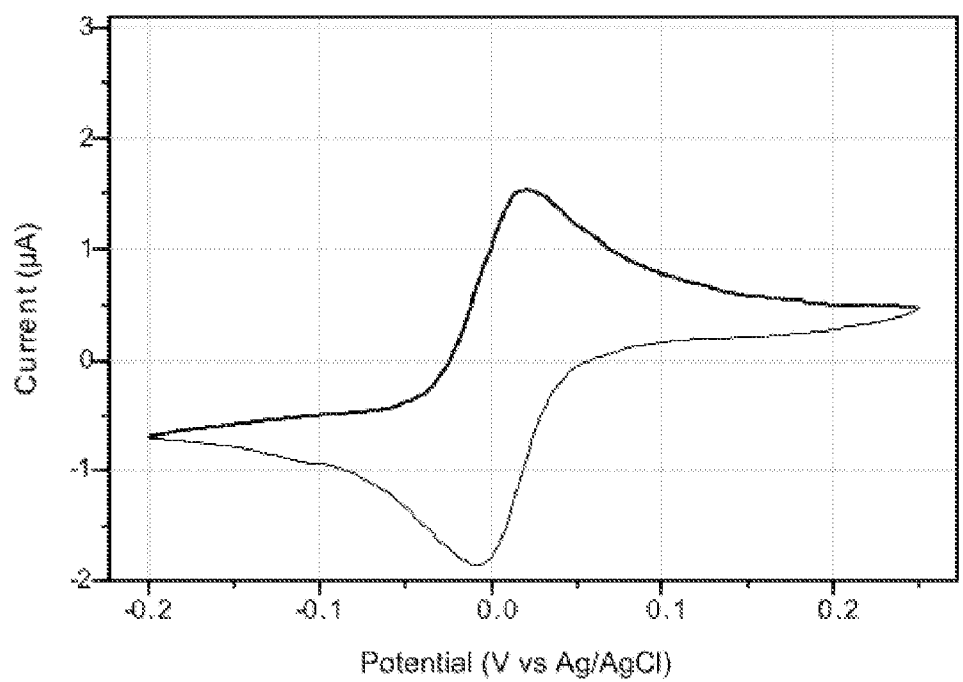
FIGS. 8 (a-f) show cyclic voltammograms measurements for a device according to the invention including 2,6-dichlorophenolindophenol as the redox mediator.
Figure 8B:
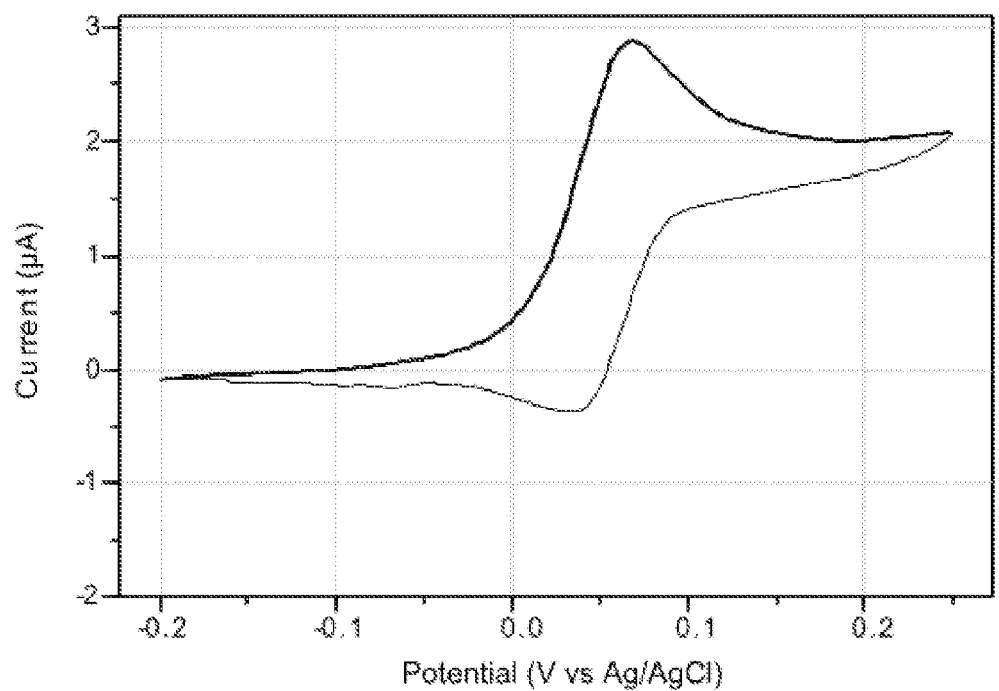
Figure 8C:
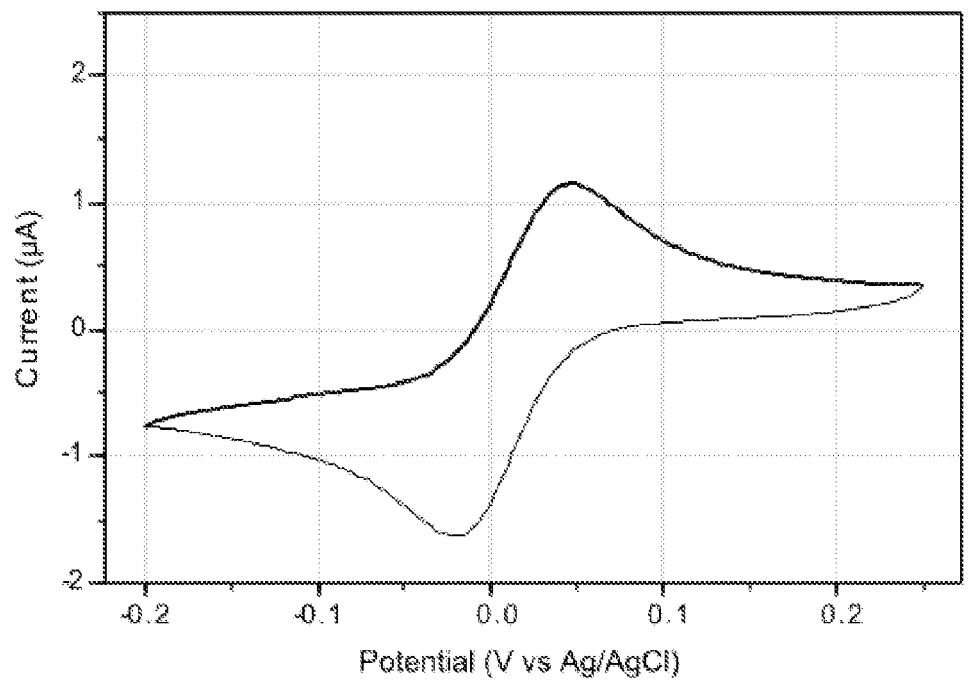
Figure 8D:
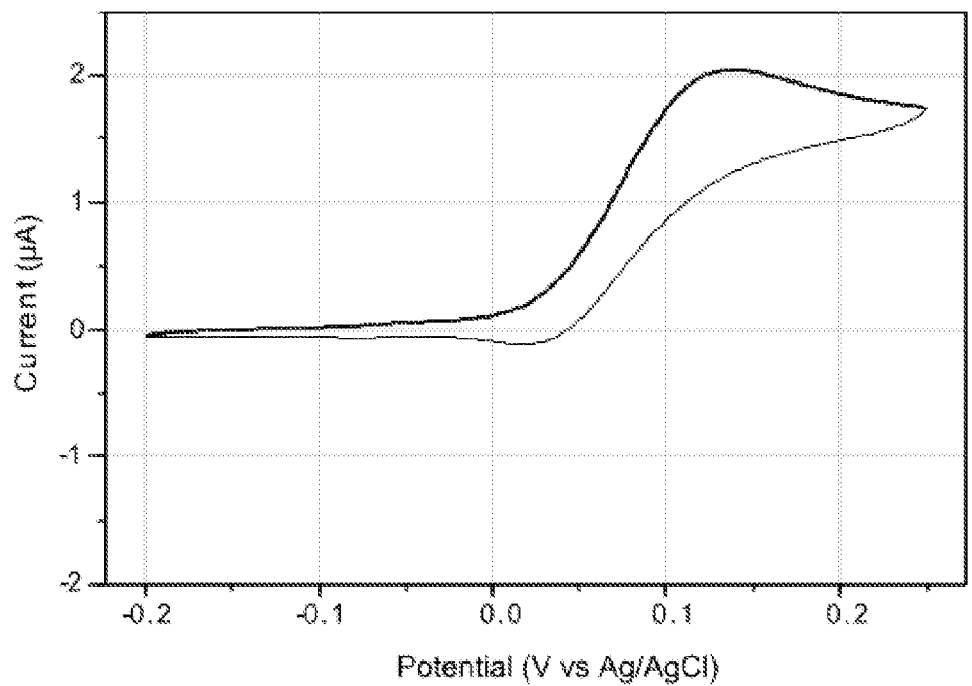
Figure 8E:
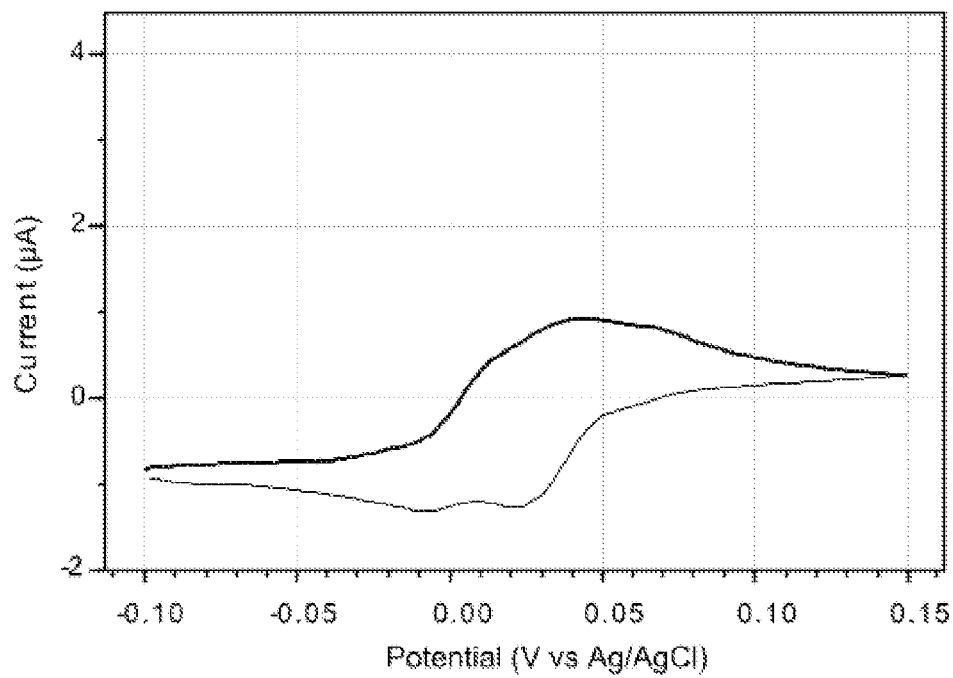
Figure 8F:
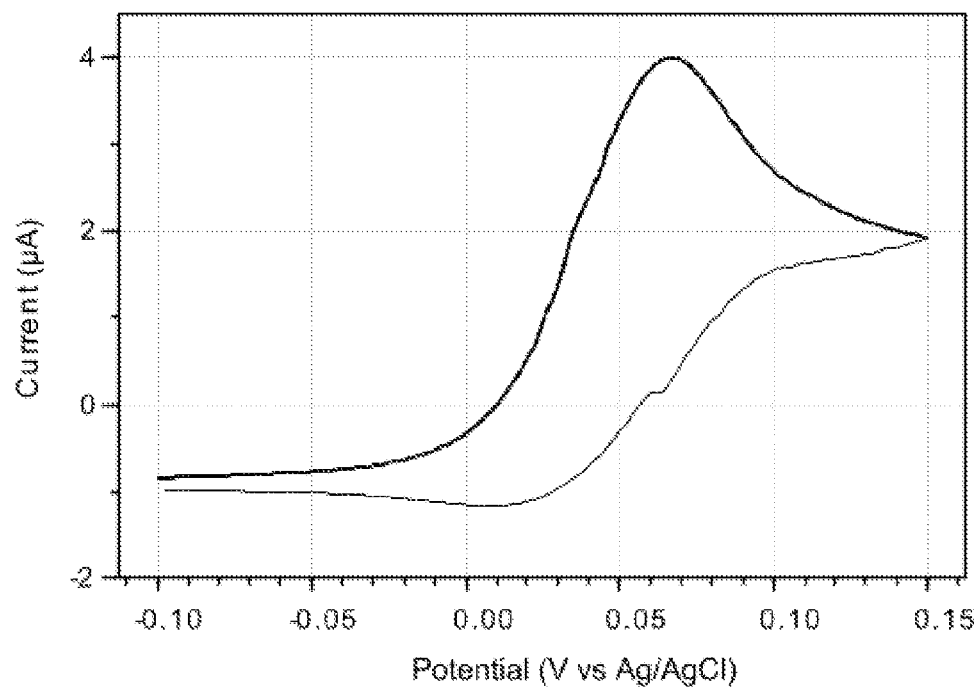

FIGS. 7a and 7b show cyclic voltammograms of feccocene carboxylic acid as the mediator with carbon (2a) and gold (2b) screen printed electrodes. FIG. 7c shows chrono amperometry plots of ferrocene carboxylic acid plus enzyme with 0, 50 micromolar and 100 micromolar arsenite.

FIGS. 8 (a-f) show cyclic voltammograms of 2,6-dichlorophenolindophenol as the mediator with carbon (a and b), gold (c and d) and carbon nanotube (e and f) screen printed electrodes, without (a,c,e) and with (b,d,f) 500 micromolar arsenite.

Figure 9:
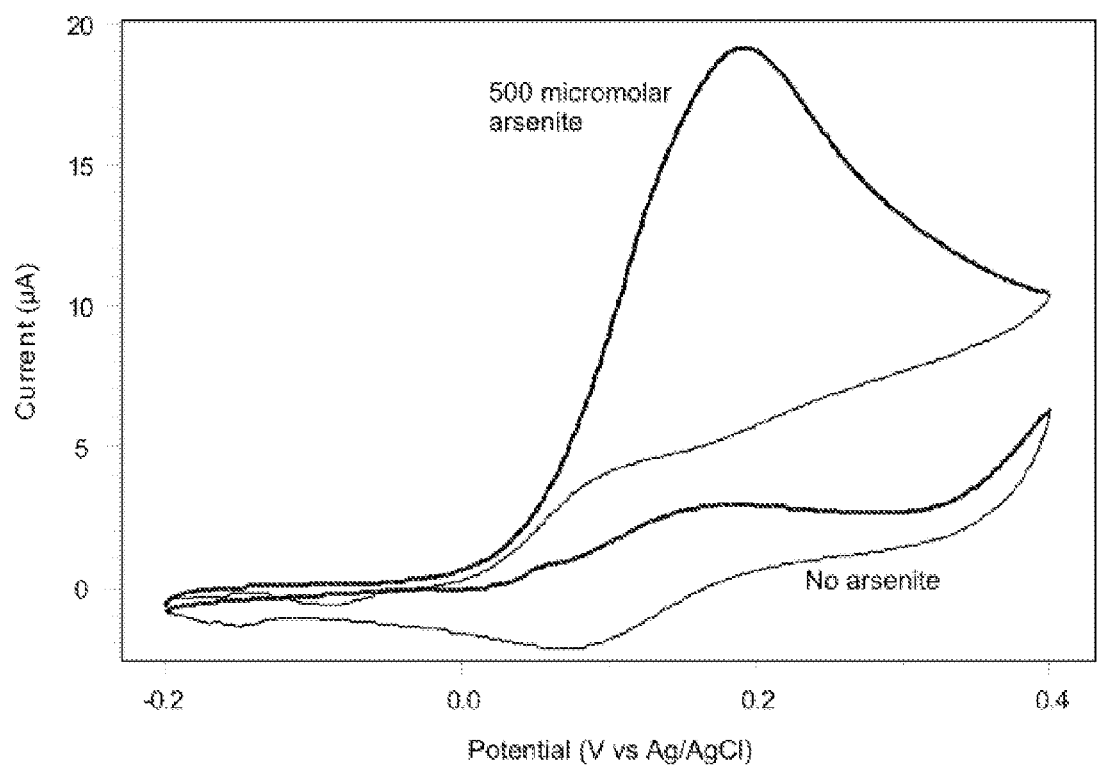
FIG. 9 shows cyclic voltammograms of TTF as the redox mediator.

FIG. 9 shows cyclic voltammograms of TTF as the mediator with carbon nanotube screen printed electrodes, without and with 500 micromolar arsenite.

Chronoamperometry plots show a shift to high current values in the presence of arsenite and there was a linear dose response in the current shift to the arsenite concentration.

The invention claimed is:

1. A device for detecting the presence of arsenite in a sample, comprising at least one electrode, a redox mediator, and an arsenite oxidase enzyme modified to prevent translocation to the periplasm, wherein the enzyme comprises [1] the native AioA subunit from NT-26, or a variant, homologue or derivative thereof having at least 90% sequence homology to the amino acid sequence of SEQ ID NO:4, and [2] the native AioB subunit from NT-26, or a variant, homologue or derivative thereof having at least 90% sequence homology to the amino acid sequence of SEQ ID NO:3, wherein a portion of the native AioB subunit corresponding to the translocation signal sequence, or a functional fragment thereof, is modified, and wherein said enzyme has arsenite oxidase activity.

2. The device according to claim 1, wherein the electrode is made of one or more conducting materials, selected from carbon, carbon nanotubes, graphene, graphite, gold, palladium, glassy carbon, nanostructured metal oxides or nanostructured metal.

3. The device according to claim 1, wherein the redox mediator is selected from metal complexes where the metal exists in two or more different redox states, comprising iron, ruthenium or osmium complexes, and organic molecules that can exist in two or more accessible redox states, comprising cytochromes, conducting organic polymers, conducting organic salts, 2, 6-dichlorophenolindophenol, ferrocene or ferrocene derivatives including ferrocene carboxylic acid and hydroxmethyl ferrocene (ferrocene methanol), Tris (2, 2'-bipyridine) dichlororuthenium (11), tetrathiafulvalene (TTF) and quinones.

4. The device according to claim 1, further comprising a reference electrode.

5. The device according to claim 4, wherein the reference electrode comprises a Ag/AgCl reference redox couple.

6. The device according to claim 1, wherein the device is a test strip with a micro-structured surface.

* * * * *

SEQUENCE LISTING

<160> NUMBER OF SEQ ID NOS: 10

<210> SEQ ID NO 1
<211> LENGTH: 175
<212> TYPE: PRT
<213> ORGANISM: Rhizobium sp. NT-26

<400> SEQUENCE: 1

Met Ser Arg Cys Gln Asn Met Val Asp Ile Gly Arg Arg Gln Phe Leu
1               5                   10                  15

Arg Gly Gly Ala Leu Ala Ala Ala Gly Ala Thr Ala Ala Val Phe Gly
            20                  25                  30

Val Gly Ala Pro Gln Ala Arg Ala Ala Thr Ala Ala Ala Gly Val Glu
        35                  40                  45

Tyr Pro Ala Asn Arg Leu Ala Asn Ile Ser Glu Leu Thr Leu Asn Glu
    50                  55                  60

Pro Leu Asp Val Ala Tyr Pro Asp Glu Asp Ala Ala Gly Val Leu Leu
65                  70                  75                  80

Lys Leu Gly Thr Arg Val Glu Gly Gly Val Gly Pro Asp Gly Asp Ile
                85                  90                  95

Val Gly Phe Ser Thr Ile Cys Pro His Lys Gly Phe Pro Leu Ser Tyr
            100                 105                 110

Ser Ala Asp Asn Lys Thr Phe Asn Cys Pro Gly His Phe Ser Val Phe
        115                 120                 125

Asp Pro Glu Lys Gly Gln Gln Val Trp Gln Ala Thr Gln Asn
    130                 135                 140

Leu Pro Gln Tyr Val Leu Arg Val Ala Asp Asn Gly Asp Ile Phe Ala
145                 150                 155                 160

Glu Gly Val Asp Glu Leu Ile Tyr Gly Arg Leu Ser Asn Val Leu
                165                 170                 175

<210> SEQ ID NO 2
<211> LENGTH: 40
<212> TYPE: PRT
<213> ORGANISM: Rhizobium sp. NT-26

<400> SEQUENCE: 2

Met Ser Arg Cys Gln Asn Met Val Asp Ile Gly Arg Arg Gln Phe Leu
1               5                   10                  15

Arg Gly Gly Ala Leu Ala Ala Ala Gly Ala Thr Ala Ala Val Phe Gly
            20                  25                  30

Val Gly Ala Pro Gln Ala Arg Ala
        35                  40

<210> SEQ ID NO 3
<211> LENGTH: 150
<212> TYPE: PRT
<213> ORGANISM: Rhizobium sp. NT-26

<400> SEQUENCE: 3

Ala Thr Ala Ala Val Phe Gly Val Gly Ala Pro Gln Ala Arg Ala Ala
1               5                   10                  15

Thr Ala Ala Ala Gly Val Glu Tyr Pro Ala Asn Arg Leu Ala Asn Ile
            20                  25                  30

Ser Glu Leu Thr Leu Asn Glu Pro Leu Asp Val Ala Tyr Pro Asp Glu
        35                  40                  45

Asp Ala Ala Gly Val Leu Leu Lys Leu Gly Thr Arg Val Glu Gly Gly
    50                  55                  60

```
Val Gly Pro Asp Gly Asp Ile Val Gly Phe Ser Thr Ile Cys Pro His
 65                  70                  75                  80

Lys Gly Phe Pro Leu Ser Tyr Ser Ala Asp Asn Lys Thr Phe Asn Cys
                 85                  90                  95

Pro Gly His Phe Ser Val Phe Asp Pro Glu Lys Gly Gly Gln Gln Val
            100                 105                 110

Trp Gly Gln Ala Thr Gln Asn Leu Pro Gln Tyr Val Leu Arg Val Ala
        115                 120                 125

Asp Asn Gly Asp Ile Phe Ala Glu Gly Val Asp Glu Leu Ile Tyr Gly
130                 135                 140

Arg Leu Ser Asn Val Leu
145                 150

<210> SEQ ID NO 4
<211> LENGTH: 845
<212> TYPE: PRT
<213> ORGANISM: Rhizobium sp. NT-26

<400> SEQUENCE: 4

Met Ala Phe Lys Arg His Ile Asp Arg Leu Pro Ile Ile Pro Ala Asp
1               5                   10                  15

Ala Lys Lys His Asn Val Thr Cys His Phe Cys Ile Val Gly Cys Gly
                20                  25                  30

Tyr His Ala Tyr Thr Trp Pro Ile Asn Lys Gln Gly Thr Asp Pro
            35                  40                  45

Gln Asn Asn Ile Phe Gly Val Asp Leu Ser Glu Gln Gln Gln Ala Glu
        50                  55                  60

Ser Asp Ala Trp Tyr Ser Pro Ser Met Tyr Asn Val Val Lys Gln Asp
 65                  70                  75                  80

Gly Arg Asp Val His Val Val Ile Lys Pro Asp His Glu Cys Val Val
                 85                  90                  95

Asn Ser Gly Leu Gly Ser Val Arg Gly Ala Arg Met Ala Glu Thr Ser
            100                 105                 110

Phe Ser Glu Ala Arg Asn Thr Gln Gln Gln Arg Leu Thr Asp Pro Leu
        115                 120                 125

Val Trp Arg Tyr Gly Gln Met Gln Pro Thr Ser Trp Asp Asp Ala Leu
130                 135                 140

Asp Leu Val Ala Arg Val Thr Ala Lys Ile Val Lys Glu Lys Gly Glu
145                 150                 155                 160

Asp Ala Leu Ile Val Ser Ala Phe Asp His Gly Gly Ala Gly Gly Gly
                165                 170                 175

Tyr Glu Asn Thr Trp Gly Thr Gly Lys Leu Tyr Phe Glu Ala Met Lys
            180                 185                 190

Val Lys Asn Ile Arg Ile His Asn Arg Pro Ala Tyr Asn Ser Glu Val
        195                 200                 205

His Gly Thr Arg Asp Met Gly Val Gly Glu Leu Asn Asn Cys Tyr Glu
210                 215                 220

Asp Ala Glu Leu Ala Asp Thr Ile Val Ala Val Gly Thr Asn Ala Leu
225                 230                 235                 240

Glu Thr Gln Thr Asn Tyr Phe Leu Asn His Trp Ile Pro Asn Leu Arg
                245                 250                 255

Gly Glu Ser Leu Gly Lys Lys Lys Glu Leu Met Pro Glu Pro His
            260                 265                 270

Glu Ala Gly Arg Ile Ile Ile Val Asp Pro Arg Arg Thr Val Thr Val
```

```
                      275                 280                 285
Asn Ala Cys Glu Gln Thr Ala Gly Ala Asp Asn Val Leu His Leu Ala
    290                 295                 300
Ile Asn Ser Gly Thr Asp Leu Ala Leu Phe Asn Ala Leu Phe Thr Tyr
305                 310                 315                 320
Ile Ala Asp Lys Gly Trp Val Asp Arg Asp Phe Ile Asp Lys Ser Thr
                325                 330                 335
Leu Arg Glu Gly Thr Ala Arg Pro Pro Leu Tyr Pro Ala Arg Gly Val
                340                 345                 350
Ser Glu Ala Asn Pro Gly His Leu Ser Ser Phe Glu Asp Ala Val Glu
                355                 360                 365
Gly Cys Arg Met Ser Ile Glu Glu Ala Ala Glu Ile Thr Gly Leu Asp
            370                 375                 380
Ala Ala Gln Ile Ile Lys Ala Ala Glu Trp Ile Gly Met Pro Lys Glu
385                 390                 395                 400
Gly Gly Lys Arg Arg Arg Val Met Phe Gly Tyr Glu Lys Gly Leu Ile
                405                 410                 415
Trp Gly Asn Asp Asn Tyr Arg Thr Asn Gly Ala Leu Val Asn Leu Ala
                420                 425                 430
Leu Ala Thr Gly Asn Ile Gly Arg Pro Gly Gly Val Val Arg Leu
            435                 440                 445
Gly Gly His Gln Glu Gly Tyr Val Arg Pro Ser Asp Ala His Val Gly
450                 455                 460
Arg Pro Ala Ala Tyr Val Asp Gln Leu Leu Ile Gly Gln Gly Gly
465                 470                 475                 480
Val His His Ile Trp Gly Cys Asp His Tyr Lys Thr Thr Leu Asn Ala
                485                 490                 495
His Glu Phe Lys Arg Val Tyr Lys Lys Arg Thr Asp Met Val Lys Asp
                500                 505                 510
Ala Met Ser Ala Ala Pro Tyr Gly Asp Arg Glu Ala Met Val Asn Ala
                515                 520                 525
Ile Val Asp Ala Ile Asn Gln Gly Gly Leu Phe Ala Val Asn Val Asp
            530                 535                 540
Ile Ile Pro Thr Lys Ile Gly Glu Ala Cys His Val Ile Leu Pro Ala
545                 550                 555                 560
Ala Thr Ser Gly Glu Met Asn Leu Thr Ser Met Asn Gly Glu Arg Arg
                565                 570                 575
Met Arg Leu Thr Glu Arg Tyr Met Asp Pro Pro Gly Gln Ser Met Pro
                580                 585                 590
Asp Cys Leu Ile Ala Ala Arg Leu Ala Asn Thr Met Glu Arg Val Leu
            595                 600                 605
Thr Glu Met Gly Asp Val Gly Tyr Ala Ala Gln Phe Lys Gly Phe Asp
            610                 615                 620
Trp Gln Thr Glu Glu Asp Ala Phe Met Asp Gly Tyr Asn Lys Asn Ala
625                 630                 635                 640
His Gly Gly Glu Phe Val Thr Tyr Glu Arg Leu Ser Ala Met Gly Thr
                645                 650                 655
Asn Gly Phe Gln Glu Pro Ala Thr Gly Phe Thr Asp Gly Lys Ile Glu
                660                 665                 670
Gly Thr Gln Arg Leu Tyr Thr Asp Gly Val Phe Ser Thr Asp Asp Gly
            675                 680                 685
Lys Ala Arg Phe Met Asp Ala Pro Trp Arg Gly Leu Gln Ala Pro Gly
            690                 695                 700
```

```
Lys Gln Gln Gln Lys Asp Ser His Lys Tyr Leu Ile Asn Asn Gly Arg
705                 710                 715                 720

Ala Asn Val Val Trp Gln Ser Ala Tyr Leu Asp Gln Glu Asn Asp Phe
                725                 730                 735

Val Met Asp Arg Phe Pro Tyr Pro Phe Ile Glu Met Asn Pro Glu Asp
            740                 745                 750

Met Ala Glu Ala Gly Leu Lys Glu Gly Asp Leu Val Glu Ile Tyr Asn
        755                 760                 765

Asp Ala Gly Ala Thr Gln Ala Met Ala Tyr Pro Thr Pro Thr Ala Arg
    770                 775                 780

Arg Gly Glu Thr Phe Met Leu Phe Gly Phe Pro Thr Gly Val Gln Gly
785                 790                 795                 800

Asn Val Thr Ser Ala Gly Thr Asn Glu Leu Ile Ile Pro Asn Tyr Lys
                805                 810                 815

Gln Thr Trp Gly Asn Ile Arg Lys Ile Ser Asp Ala Pro Arg Asn Val
            820                 825                 830

Ala His Leu Ser Phe Lys Ser Lys Glu Tyr Gln Ser Ala
        835                 840                 845
```

<210> SEQ ID NO 5
<211> LENGTH: 528
<212> TYPE: DNA
<213> ORGANISM: Rhizobium sp. NT-26

<400> SEQUENCE: 5

```
atgtcacgtt gtcaaaacat ggtcgatatt ggccgacgcc agttcctgcg tggaggcgcg    60
ctcgcggctg cgggtgcgac tgccgccgtc ttcggcgtcg gcgcaccaca ggctagagcc   120
gctaccgcgg cggcagggt cgaatatcct gccaatcgtc tggcaaacat ctcagaactt   180
acgctcaatg aaccgctcga tgtcgcctat ccggacgagg atgccgcagg cgttctgctt   240
aagcttggga cccgcgtcga gggtggcgtt ggccctgacg gcgacattgt cggcttttcc   300
acgatctgtc ctcacaaggg ttttcctctg agctactccg ccgacaacaa gacgttcaac   360
tgtcctggtc acttctcggt cttcgaccct gaaaagggcg ccagcaggt ttggggtcag   420
gccacgcaga acctgccgca atacgtgctc cgcgtcgccg acaatggcga catctttgcc   480
gaaggcgtcg acgagctgat ctacggccgt ctgtccaacg ttctataa                528
```

<210> SEQ ID NO 6
<211> LENGTH: 120
<212> TYPE: DNA
<213> ORGANISM: Rhizobium sp. NT-26

<400> SEQUENCE: 6

```
atgtcacgtt gtcaaaacat ggtcgatatt ggccgacgcc agttcctgcg tggaggcgcg    60
ctcgcggctg cgggtgcgac tgccgccgtc ttcggcgtcg gcgcaccaca ggctagagcc   120
```

<210> SEQ ID NO 7
<211> LENGTH: 408
<212> TYPE: DNA
<213> ORGANISM: Rhizobium sp. NT-26

<400> SEQUENCE: 7

```
gctaccgcgg cggcagggt cgaatatcct gccaatcgtc tggcaaacat ctcagaactt    60
acgctcaatg aaccgctcga tgtcgcctat ccggacgagg atgccgcagg cgttctgctt   120
aagcttggga cccgcgtcga gggtggcgtt ggccctgacg gcgacattgt cggcttttcc   180
```

| | |
|---|---|
| acgatctgtc ctcacaaggg ttttcctctg agctactccg ccgacaacaa gacgttcaac | 240 |
| tgtcctggtc acttctcggt cttcgaccct gaaaagggcg gccagcaggt ttggggtcag | 300 |
| gccacgcaga acctgccgca atacgtgctc cgcgtcgccg acaatggcga catctttgcc | 360 |
| gaaggcgtcg acgagctgat ctacggccgt ctgtccaacg ttctataa | 408 |

<210> SEQ ID NO 8
<211> LENGTH: 2538
<212> TYPE: DNA
<213> ORGANISM: Rhizobium sp. NT-26

<400> SEQUENCE: 8

| | |
|---|---|
| atggccttca acgtcacat cgaccgtctg ccgatcattc ccgcggacgc caagaagcac | 60 |
| aatgtcacct gccacttctg catcgtcggt tgcggctatc acgcctatac ctggccgatc | 120 |
| aacaaacaag gcggtacgga tccacagaac aacatcttcg gcgtcgacct gtctgaacag | 180 |
| cagcaggcgg aaagcgacgc ctggtattca ccgtccatgt acaacgtggt caagcaggat | 240 |
| ggccgcgacg ttcatgtcgt catcaagcca gaccacgaat gtgtcgtgaa ctccggtctc | 300 |
| ggttcggtgc gtggcgcccg catggcagag acgagcttct cagaggcccg caacacccag | 360 |
| cagcagcgcc tcaccgatcc gcttgtctgg cgatacgggc agatgcaacc gacgagctgg | 420 |
| gacgacgcgc tcgatctcgt cgctcgcgtg accgcgaaga tcgtcaaaga aagggtgag | 480 |
| gacgccctca tcgtatcggc cttttgaccat ggcggtgcag gcggcggcta cgagaacacc | 540 |
| tggggcacgg gaaagctcta tttcgaggcc atgaaggtca agaacatccg catccacaac | 600 |
| cgcccggcct acaattccga ggttcacggc acccgcgaca tgggcgtcgg cgagttgaat | 660 |
| aactgctacg aggatgccga actgccgac acgatcgttg cggttggcac caacgcgctg | 720 |
| gagacccaga ccaactactt cctaaatcac tggattccga atctgcgcgg cgaaagcctc | 780 |
| ggcaagaaaa aggagctcat gccggaggag ccccatgaag caggcaggat cattatcgtc | 840 |
| gatccgcgcc gcaccgtgac ggtcaatgcc tgcgagcaga cggccggcgc cgacaatgtc | 900 |
| ctgcatcttg ctatcaattc tggcacggac ctcgcccttt tcaacgcact cttcacctat | 960 |
| atcgccgaca agggctgggt cgatcgcgac ttcatcgaca agtcgacact gcgcgagggt | 1020 |
| acagcccgac cgccgctcta tcctgcccgt ggagtgtcag aggccaatcc ggggcatctc | 1080 |
| tcgagtttcg aggacgccgt ggaaggctgc cgcatgtcta tcgaggaggc tgcggaaatc | 1140 |
| accggtctcg acgccgccca gatcatcaag gcagccgagt ggatcggcat gccaaggaa | 1200 |
| ggcggcaagc gccgccgtgt catgttcggt tacgagaagg gtctgatctg ggcaatgac | 1260 |
| aactaccgaa ccaacggcgc gctggtgaac ctcgcccttg ccaccggcaa tatcggccgt | 1320 |
| cccgtggcg cgtcgtacg ccttggcgga caccaggaag ctatgtgcg cccctccgac | 1380 |
| gcccatgtcg gccggccggc ggcctatgtc gaccagttgc tgatcggcgg ccagggcggc | 1440 |
| gttcaccaca tctggggctg cgaccactac aaaacgacgc tcaatgcgca tgagtttaag | 1500 |
| cgcgtctaca agaagcgcac cgacatggtg aaggacgcca tgagcgctgc ccctacggc | 1560 |
| gaccgcgagg ccatggtcaa tgccattgtc gacgcaatca atcagggcgg attgtttgcc | 1620 |
| gtcaatgtcg acatcatccc gacaaaaatc ggcgaagcct gtcatgttat ctgcctgcg | 1680 |
| gccacgtcag gcgagatgaa cctcacgtca atgaatggcg agcggcgcat gcggctgacc | 1740 |
| gaacgctata tggacccgcc cggtcagtcc atgccggact gcctgattgc cgctcgtctc | 1800 |
| gccaacacca tggaacgcgt gctgaccgag atgggtgacg tcggctatgc cgctcaattc | 1860 |

```
aagggctttg actggcagac agaagaagac gccttcatgg acggctacaa caagaatgca    1920
catggcggag agttcgtcac ctatgagcgc ctgagtgcga tgggcaccaa cggcttccag    1980
gagccggcta ccggctttac cgacggcaag atcgagggca cccagcggct ctataccgac    2040
ggcgtattct cgaccgacga cggcaaggcg cggttcatgg acgcgccatg gcggggactt    2100
caggcaccgg gcaagcagca gcagaaggac agccacaagt acttgatcaa caacggccgt    2160
gccaatgtcg tctggcaatc ggcgtatctc gaccaggaaa acgacttcgt catggatcgt    2220
ttcccctacc cgttcatcga gatgaaccca gaggacatgg cggaagcagg ccttaaggag    2280
ggcgacctcg tcgagattta caatgatgcc ggagcgacgc aggccatggc ctatccgacg    2340
ccgacagccc gacgtggaga aaccttcatg ctgttcggtt ttccaaccgg ggttcagggc    2400
aatgtgacca gtgccgggac gaacgagttg ataatcccga actacaagca gacctggggc    2460
aatatccgca agatttcgga tgcgcccagg aacgtggctc acctttcctt caagtcgaaa    2520
gaataccagt cggcttga                                                  2538

<210> SEQ ID NO 9
<211> LENGTH: 31
<212> TYPE: DNA
<213> ORGANISM: Artificial Sequence
<220> FEATURE:
<223> OTHER INFORMATION: Synthetic primer sequence

<400> SEQUENCE: 9
gcgaattcaa gctaccgcgg cggcaggggt c                                    31

<210> SEQ ID NO 10
<211> LENGTH: 32
<212> TYPE: DNA
<213> ORGANISM: Artificial Sequence
<220> FEATURE:
<223> OTHER INFORMATION: Synthetic primer sequence

<400> SEQUENCE: 10
gcctgcagtc aagccgactg gtattctttc ga                                   32
```